(12) United States Patent
Biffi et al.

(10) Patent No.: US 12,000,843 B2
(45) Date of Patent: Jun. 4, 2024

(54) COMPOSITIONS AND METHODS FOR DIAGNOSING AND TREATING PEROXISOMAL DISEASES

(71) Applicants: CHILDREN'S MEDICAL CENTER CORPORATION, Boston, MA (US); OSPEDALE SAN RAFFAELE S.R.L., Milan (IT); DANA-FARBER CANCER INSTITUTE, INC., Boston, MA (US); Fondazione Telethon, Rome (IT)

(72) Inventors: Alessandra Biffi, Boston, MA (US); Eleonora Cavalca, Milan (IT)

(73) Assignees: Children's Medical Center Corporation, Boston, MA (US); Ospedale San Raffaele S.R.L., Milan (IT); Dana-Farber Cancer Institute, Inc., Boston, MA (US); Fondazione Telethon, Rome (IT)

(*) Notice: Subject to any disclaimer, the term of this patent is extended or adjusted under 35 U.S.C. 154(b) by 1131 days.

(21) Appl. No.: 16/477,812

(22) PCT Filed: Jan. 16, 2018

(86) PCT No.: PCT/US2018/013908
§ 371 (c)(1),
(2) Date: Jul. 12, 2019

(87) PCT Pub. No.: WO2018/136434
PCT Pub. Date: Jul. 26, 2018

(65) Prior Publication Data
US 2020/0278356 A1  Sep. 3, 2020

Related U.S. Application Data

(60) Provisional application No. 62/447,346, filed on Jan. 17, 2017.

(51) Int. Cl.
| | | |
|---|---|---|
| G01N 33/68 | (2006.01) | |
| A61K 9/00 | (2006.01) | |
| A61K 35/28 | (2015.01) | |
| A61K 35/76 | (2015.01) | |

(52) U.S. Cl.
CPC ....... *G01N 33/6893* (2013.01); *A61K 9/0019* (2013.01); *A61K 9/0085* (2013.01); *A61K 35/28* (2013.01); *A61K 35/76* (2013.01); *G01N 2333/825* (2013.01); *G01N 2800/04* (2013.01); *G01N 2800/50* (2013.01)

(58) Field of Classification Search
CPC ......... G01N 33/6893; G01N 2333/825; G01N 2800/04; G01N 2800/50; A61K 9/0019; A61K 9/0085; A61K 35/28; A61K 35/76
See application file for complete search history.

(56) References Cited

U.S. PATENT DOCUMENTS

| | | |
|---|---|---|
| 6,537,785 B1 | 3/2003 | Canfield |
| 8,093,209 B2 | 1/2012 | Laskowitz et al. |
| 9,339,512 B2 | 5/2016 | Widdowson et al. |
| 2001/0038836 A1 | 11/2001 | During et al. |
| 2004/0067500 A1 | 4/2004 | Gould-Rothberg et al. |
| 2007/0009500 A1 | 1/2007 | Blazar et al. |
| 2007/0081992 A1 | 4/2007 | Pardridge et al. |
| 2008/0254017 A1 | 10/2008 | Kane et al. |
| 2009/0318333 A1 | 12/2009 | Vallee |
| 2010/0151573 A1 | 6/2010 | King et al. |
| 2010/0166759 A1 | 7/2010 | Berezin et al. |
| 2010/0221225 A1 | 9/2010 | Byrne et al. |
| 2010/0233084 A1 | 9/2010 | Narasimhaswamy et al. |
| 2011/0223127 A1 | 9/2011 | Purschke et al. |
| 2012/0003202 A1 | 1/2012 | Calias et al. |
| 2014/0017212 A1 | 1/2014 | Rebar |
| 2014/0235697 A1 | 8/2014 | Weiner et al. |
| 2015/0223436 A1 | 8/2015 | Rossi et al. |
| 2016/0256492 A1 | 9/2016 | Naldini et al. |
| 2017/0333527 A1 | 11/2017 | Fukuta et al. |
| 2018/0161357 A1 | 6/2018 | Jackson et al. |
| 2018/0187156 A1 | 7/2018 | Rossi et al. |
| 2019/0367584 A1 | 12/2019 | Biffi et al. |
| 2020/0038439 A1 | 2/2020 | Biffi et al. |

FOREIGN PATENT DOCUMENTS

| | | |
|---|---|---|
| JP | 2007051980 A | 3/2007 |
| JP | 2008534529 A | 8/2008 |
| JP | 2015527083 A | 9/2015 |
| KR | 101625755 B1 | 5/2016 |

(Continued)

OTHER PUBLICATIONS

Cesani, et al, "Metallothioneins as Dynamic Markers for Brain Disease in Lysosomal Disorders," Annals Neurology, Jan. 1, 2014, vol. 75, pp. 127-137.
International Search Report and Written Opinion in corresponding PCT Patent Application No. PCT/US2018/013908, dated Jun. 14, 2018 (10 pages).
Ito et al., "The Potential Roles of Metallothionein as a Therapeutic Target for Cerebral Ischemia and Retinal Diseases," Current Pharmaceutical Biotechnology, 2013, vol. 14, No. 4, pp. 400-407.
Jeyakumar et al., "Central nervous system inflammation is a hallmark of pathogenesis in mouse models of GM1 and GM2 gangliosidosis," Brain, 2003, vol. 126, pp. 974-987.
Kemp et al., "ABCD1 Mutations and the X-linked Adrenoleukodystrophy Mutation Database: Role in Diagnosis and Clinical Correlations," Human Mutation, 2001, vol. 18, pp. 499-515.

(Continued)

*Primary Examiner* — Olga N Chernyshev
(74) *Attorney, Agent, or Firm* — Melissa Hunter-Ensor; Nathan Hsu; Greenberg Traurig, LLP

(57) ABSTRACT

The invention features compositions and methods for the treatment and prevention of peroxisomal diseases (e.g., neonatal adrenoleukodystrophy and Zellweger syndrome), including in a subject selected as having increased levels of metallothionein polypeptides. The invention also provides compositions and methods for identifying a subject having a peroxisomal disease involving detecting metallothionein polypeptides or polynucleotides.

6 Claims, 2 Drawing Sheets

Specification includes a Sequence Listing.

(56) References Cited

FOREIGN PATENT DOCUMENTS

| | | |
|---|---|---|
| WO | 1996002670 A1 | 2/1996 |
| WO | 2000029846 A2 | 5/2000 |
| WO | 2000073482 A1 | 12/2000 |
| WO | 2002096439 A1 | 12/2002 |
| WO | 2004015089 A2 | 2/2004 |
| WO | 2006102933 A1 | 10/2006 |
| WO | 2010012667 A1 | 2/2010 |
| WO | 2013030785 A1 | 3/2013 |
| WO | 2014039745 A1 | 3/2014 |
| WO | 2015164750 A2 | 10/2015 |
| WO | 2016039163 A1 | 3/2016 |
| WO | 2016094880 A1 | 6/2016 |

OTHER PUBLICATIONS

Kemper et al., "Newborn screening for X-linked adrenoleukodystrophy: evidence summary and advisory committee recommendation," Genetics in Medicine, Jan. 2017, vol. 19, No. 1, pp. 121-126.

Kimura et al., "Function of Metallothionein in Gene Expression and Signal Transduction: Newly Found Protective Role of Metallothionein," Journal of Health Science, 2008, vol. 54, No. 3, pp. 251-260.

Kuo et al., "Theoretical and practical applications of the intracerebroventricular route for CSF sampling and drug administration in CNS drug discovery research: A mini review," Journal of Neuroscience Methods, 2014, vol. 233, pp. 166-171.

Layre et al., "Novel composite core-shell nanoparticles as busulfan carriers," Journal of Controlled Release, 2006, vol. 111, No. 3, pp. 271-280.

Lin et al., "Mitigation of cerebellar neuropathy in globoid cell leukodystrophy mice by AAV-mediated gene therapy," Gene, 2015, vol. 571, No. 1, pp. 81-90.

"Lysosomal storage diseases," downloaded from Lysosomal storage disease—Wikipedia on Feb. 22, 2022, pp. 1-8.

Macauley et al., "Cerebellar Pathology and Motor Deficits in the Palmitoyl Protein Thioesterase 1-Deficient Mouse," Experimental Neurology, May 2009, vol. 217, No. 1, pp. 124-135.

Manso et al., "Overexpression of Metallothionein-1 Modulates the Phenotype of the Tg2576 Mouse Model of Alzheimer's Disease," Journal of Alzheimer's Disease, 2016, vol. 51, No. 1, pp. 81-95.

Matcovitch-Natan et al., "Microglia development follows a stepwise program to regulate brain homeostasis," Science, Aug. 19, 2016, vol. 353, No. 6301, p. 789, aad8670 pp. 1-12.

Matzner et al., "Enzyme replacement improves nervous system pathology and function in a mouse model for metachromatic leukodystrophy," Human Molecular Genetics, 2005, vol. 14, No. 9, pp. 1139-1152.

Mildner et al., "Microglia in the adult brain arise from Ly-6ChiCCR2+ monocytes only under defined host conditions," Nature Neuroscience, Dec. 2007, vol. 10, No. 12, pp. 1544-1553.

Miller et al., "Outcomes after allogeneic hematopoietic cell transplantation for childhood cerebral adrenoleukodystrophy: the largest single-institution cohort report," Blood, Aug. 18, 2011, vol. 118, No. 7, pp. 1971-1978.

Miyamoto et al., "Microglia and synapse interactions: fine tuning neural circuits and candidate molecules," Frontiers In Cellular Neuroscience, May 15, 2013, vol. 7, Article No. 70, pp. 1-6.

Moser, Hugo W., "Adrenoleukodystrophy: phenotype, genetics, pathogenesis and therapy," Brain, Aug. 1997, vol. 120, No. 8, pp. 1485-1508.

Musolino et al., "Hematopoietic Stem Cell Transplantation in the Leukodystrophies: A Systematic Review of the Literature," Neuropediatrics, Jun. 2014, vol. 45, No. 3, pp. 169-174.

Nakao et al., "Atypical expression of circadian clock genes in denervated mouse skeletal muscle," Chronobiology International, 2015, vol. 32, No. 4, pp. 486-496.

Nicaise et al., "A Microglial Hypothesis of Globoid Cell Leukodystrophy Pathology," Journal of Neuroscience Research, Nov. 2016, vol. 94, No. 11, pp. 1049-1061.

Ohmi et al., "Activated microglia in cortex of mouse models of mucopolysaccharidoses I and IIIB," Proceedings of the National Academy of Sciences of the United States of America, Feb. 18, 2003, vol. 100, No. 4, pp. 1902-1907.

Pachiappan et al., "Glial inflammation and neurodegeneration induced by candoxin, a novel neurotoxin from Bungarus candidus venom: global gene expression analysis using microarray," Toxicon, 2005, vol. 46, No. 8, pp. 883-899.

Palmiter et al., "Distal Regulatory Elements from the Mouse Metallothionein Locus Stimulate Gene Expression in Transgenic Mice," Molecular and Cellular Biology, Sep. 1993, vol. 13, No. 9, pp. 5266-5275.

Perego et al., "Temporal pattern of expression and colocalization of microglia/macrophage phenotype markers following brain ischemic injury in mice," Journal of Neuroinflammation, 2011, vol. 8, Article No. 174, pp. 1-19.

Peviani et al., "Unraveling the Complexity of Amyotrophic Lateral Sclerosis: Recent Advances from the Transgenic Mutant SOD1 Mice," CNS & Neurological Disorders—Drug Targets, 2010, vol. 9, No. 4, pp. 491-503.

Platt, Frances M., "Sphingolipid lysosomal storage disorders," Nature, Jun. 5, 2014, vol. 510, pp. 68-75.

Rettig et al., "Mobilization of hematopoietic stem and progenitor cells using inhibitors of CXCR4 and VLA-4," Leukemia, 2012, vol. 26, pp. 34-53.

Rojo et al., "Redox Control of Microglial Function: Molecular Mechanisms and Functional Significance," Antioxidants & Redox Signaling, 2014, vol. 21, No. 12, pp. 1766-1801.

Sessa et al., "Lentiviral haemopoietic stem-cell gene therapy in early-onset metachromatic leukodystrophy: an ad-hoc analysis of a non-randomised, open-label, phase 1/2 trial," The Lancet, Elsevier, Amsterdam, NL, Jun. 8, 2016, vol. 388, No. 10043, pp. 476-487.

Settembre et al., "Signals for the lysosome: a control center for cellular clearance and energy metabolism," Nature Reviews: Molecular Cell Biology, May 2013, vol. 14, No. 5, pp. 283-296.

Sharma et al., "Biomarkers in Parkinson's disease (recent update)," Neurochemistry International, 2013, vol. 63, No. 3, pp. 201-229.

Simard et al., "Bone Marrow-Derived Microglia Play a Critical Role in Restricting Senile Plaque Formation in Alzheimer's Disease," Neuron, Feb. 16, 2006, vol. 49, pp. 489-502.

Subramanian et al., "Gene set enrichment analysis: A knowledge-based approach for interpreting genome-wide expression profiles," Proceedings of the National Academy of Sciences of the United States of America, Oct. 25, 2005, vol. 102, No. 43, pp. 15545-15550.

Sugiyama et al., "Maintenance of the Hematopoietic Stem Cell Pool by CXCL12-CXCR4 Chemokine Signaling in Bone Marrow Stromal Cell Niches," Immunity, Dec. 2006, vol. 25, pp. 977-988.

Tay et al., "Microglia across the lifespan: from origin to function in brain development, plasticity and cognition," The Journal of Physiology, 2017, vol. 595, No. 6, pp. 1929-1945.

Tokuda et al., "Overexpression of metallothionein-I, a copper-regulating protein, attenuates intracellular copper dyshomeostasis and extends lifespan in a mouse model of amyotrophic lateral sclerosis caused by mutant superoxide dismutase-1," Human Molecular Genetics, 2014, vol. 23, No. 5, pp. 1271-1285.

Turner et al., "Evidence of widespread cerebral microglial activation in amyotrophic lateral sclerosis: an [11C](R)-PK11195 positron emission tomography study," Neurobiology of Disease, 2004, vol. 15, pp. 601-609.

Vela et al., "Induction of metallothionein in astrocytes and microglia in the spinal cord from the myelin-deficient jimpy mouse," Brain Research, 1997, vol. 767, pp. 345-355.

Villani et al., "Cytokines, Neurotrophins, and Oxidative Stress in Brain Disease From Mucopolysaccharidosis IIIB," Journal of Neuroscience Research, 2007, vol. 85, No. 3, pp. 612-622.

Visigalli et al., "Gene therapy augments the efficacy of hematopoietic cell transplantation and fully corrects mucopolysaccharidosis type I phenotype in the mouse model," Blood, Dec. 9, 2010, vol. 116, No. 24, pp. 5130-5139.

(56) References Cited

OTHER PUBLICATIONS

Visigalli et al., "Monitoring disease evolution and treatment response in lysosomal disorders by the peripheral benzodiazepine receptor ligand PK11195," Neurobiology of Disease, 2009, vol. 34, pp. 51-62.

Wada et al., "Microglial activation precedes acute neurodegeneration in Sandhoff disease and is suppressed by bone marrow transplantation," Proceedings of the National Academy of Sciences of the United States of America, Sep. 26, 2000, vol. 97, No. 20, pp. 10954-10959.

Wang et al., "Metallothionein Inhibits Doxorubicin-Induced Mitochondrial Cytochrome c Release and Caspase-3 Activation in Cardiomyocytes," The Journal of Pharmacology and Experimental Therapeutics, 2001, vol. 298, No. 2, pp. 461-468.

Wang et al., "Translocator protein (Tspo) gene promoter-driven green fluorescent protein synthesis in transgenic mice: an in vivo model to study Tspo transcription," Cell and Tissue Research, Nov. 2012, vol. 350, No. 2, pp. 261-275.

West et al., "Metallothionein in the central nervous system: roles in protection, regeneration and cognition," Neurotoxicology, May 2008, vol. 29, No. 3, pp. 488-502.

Wiesinger et al., "The genetic landscape of X-linked adrenoleukodystrophy: inheritance, mutations, modifier genes, and diagnosis," The Application of Clinical Genetics, 2015, vol. 8, pp. 109-121.

Wilkinson et al., "Busulfan Conditioning Enhances Engraftment of Hematopoietic Donor-derived Cells in the Brain Compared With Irradiation," Molecular Therapy, Apr. 2013, vol. 21, No. 4, pp. 868-876.

Atagi et al., "Apolipoprotein E Is a Ligand for Triggering Receptor Expressed on Myeloid Cells 2 (TREM2)," Journal of Biological Chemistry, Oct. 23, 2015, vol. 290, No. 43, pp. 26043-26050.

Qi et al., "Myricitrin Modulates NADPH Oxidase-Dependent ROS Production to Inhibit Endotoxin-Mediated Inflammation by Blocking the JAK/STAT1 and NOX2/p47phox Pathways," Oxidative Medicine and Cellular Longevity, Jun. 20, 2017, vol. 2017, Article ID 9738745, pp. 1-20.

Yu et al., "Metallothionein III is reduced in Alzheimer's disease," Brain Research, Mar. 9, 2001, vol. 894, No. 1, pp. 37-45.

International Search Report and Written Opinion issued in International Patent Application No. PCT/US20/53826, dated Feb. 9, 2021 (18 pages).

International Search Report and Written Opinion issued in International Patent Application No. PCT/US20/53824, dated Mar. 22, 2021 (21 pages).

Ajami et al., "Infiltrating monocytes trigger EAE progression, but do not contribute to the resident microglia pool," Nature Neuroscience, Sep. 2011, vol. 14, No. 9, pp. 1142-1149.

Ajami et al., "Local self-renewal can sustain CNS microglia maintenance and function throughout adult life," Nature Neuroscience, Dec. 2007, vol. 10, No. 12, pp. 1538-1543.

Ambjorn et al., "Metallothionein and a peptide modeled after metallothionein, EmtinB, induce neuronal differentiation and survival through binding to receptors of the low-density lipoprotein receptor family," Journal of Neurochemistry, 2008, vol. 104, pp. 21-37.

Andrews, Glen K., "Regulation of Metallothionein Gene Expression by Oxidative Stress and Metal Ions," Biochemical Pharmacology, 2000, vol. 59, pp. 95-104.

Aronovich et al., "Lysosomal storage disease: Gene therapy on both sides of the blood-brain barrier," Molecular Genetics and Metabolism, Feb. 2015, vol. 114, No. 2, pp. 83-93.

Aubourg et al., "Reversal of Early Neurologic and Neuroradiologic Manifestations of X-linked Adrenoleukodystrophy by Bone Marrow Transplantation," The New England Journal of Medicine, Jun. 28, 1990, vol. 322, No. 26, pp. 1860-1866.

Baird et al., "Metallothionein protects against oxidative stress-induced lysosomal destabilization," Biochemical Journal, 2006, vol. 394, pp. 275-283.

Banati et al., "Positron emission tomography and functional characterization of a complete PBR/TSPO knockout," Nature Communications, Nov. 19, 2014, vol. 5, Article No. 5452, pp. 1-12.

Bennett et al., "New tools for studying microglia in the mouse and human CNS," Proceedings of the National Academy of Sciences of the United States of America, Feb. 16, 2016, vol. 113, pp. E1738-E1746.

Biffi, Alessandra, "Gene therapy for lysosomal storage disorders: a good start," Human Molecular Genetics, 2016, vol. 25, No. R1, pp. R65-R75.

Biffi et al., "Correction of metachromatic leukodystrophy in the mouse model by transplantation of genetically modified hematopoietic stem cells," The Journal of Clinical Investigation, Apr. 2004, vol. 113, No. 8, pp. 1118-1129.

Biffi et al., "Lentiviral Hematopoietic Stem Cell Gene Therapy Benefits Metachromatic Leukodystrophy," Science, American Association for the Advancement of Science, Jul. 11, 2013, pp. 1-16.

Biffi et al., "Gene therapy for leukodystrophies," Human Molecular Genetics, 2011, vol. 20, No. R1, pp. R42-R53.

Biffi et al., "Gene therapy of metachromatic leukodystrophy reverses neurological damage and deficits in mice," The Journal of Clinical Investigation, Nov. 2006, vol. 116, No. 11, pp. 3070-3082.

Butovsky et al., "Identification of a Unique TGF-β Dependent Molecular and Functional Signature in Microglia," Nature Neuroscience, Jan. 2014, vol. 17, No. 1, pp. 131-143.

Cai et al., "Zinc- or cadmium-pre-induced metallothionein protects human central nervous system cells and astrocytes from radiation-induced apoptosis," Toxicology Letters, 2004, vol. 146, No. 3, pp. 217-226.

Capotondo et al., "Brain conditioning is instrumental for successful microglia reconstitution following hematopoietic stem cell transplantation," Proceedings of the National Academy of Sciences of the United States of America, Sep. 11, 2012, vol. 109, No. 37, pp. 15018-15023.

Cartier et al., "Hematopoietic Stem Cell Gene Therapy with a Lentiviral Vector in X-Linked Adrenoleukodystrophy," Science, Nov. 6, 2009, vol. 326, pp. 818-823.

Cavalca et al., "Metallothioneins are neuroprotective agents in lysosomal storage disorders," Annals of Neurology, Feb. 2018, vol. 83, No. 2, pp. 418-432.

Cesani et al., "Characterization of New Arylsulfatase a Gene Mutations Reinforces Genotype-Phenotype Correlation In Metachromatic Leukodystrophy," Human Mutation, 2009, vol. 30, pp. E936-E945.

Chimienti et al., "Zinc resistance impairs sensitivity to oxidative stress in hela cells: protection through metallothioneins expression," Free Radical Biology & Medicine, 2001, vol. 31, No. 10, pp. 1179-1190.

Chiu et al., "A Neurodegeneration-Specific Gene-Expression Signature of Acutely Isolated Microglia from an Amyotrophic Lateral Sclerosis Mouse Model," Cell Reports, Jul. 25, 2013, vol. 4, pp. 385-401.

Chung et al., "New insight into the molecular pathways of metallothionein-mediated neuroprotection and regeneration," Journal of Neurochemistry, 2008, vol. 104, pp. 14-20.

Chung et al., "Redefining the Role of Metallothionein within the Injured Brain: Extracellular Metallothioneins Play an Important Role in the Astrocyte-Neuron Response to Injury," The Journal of Biological Chemistry, May 30, 2008, vol. 283, No. 22, pp. 15349-15358.

Colonna et al., "Microglia Function in the Central Nervous System During Health and Neurodegeneration," Annual Review of Immunology, 2017, vol. 35, pp. 441-468.

Comes et al., "Influence of Transgenic Metallothionein-1 on Gliosis, CA1 Neuronal Loss, and Brain Metal Levels of the Tg2576 Mouse Model of Alzheimer's Disease," International Journal of Molecular Sciences, 2017, vol. 18, Article No. 251, pp. 1-12.

Dar et al., "Mutual, reciprocal SDF-1/CXCR4 interactions between hematopoietic and bone marrow stromal cells regulate human stem cell migration and development in NOD/SCID chimeric mice," Experimental Hematology, 2006, vol. 34, pp. 967-975.

(56) References Cited

OTHER PUBLICATIONS

Deverman et al., "Cre-dependent selection yields AAV variants for widespread gene transfer to the adult brain," Nature Biotechnology, Feb. 2016, vol. 34, No. 2, pp. 204-209.
Di Foggia et al., "Bmi1 enhances skeletal muscle regeneration through MT1-mediated oxidative stress protection in a mouse model of dystrophinopathy," Journal of Experimental Medicine, 2014, vol. 211, No. 13, pp. 2617-2633.
Ebadi et al., "Metallothionein-mediated neuroprotection in genetically engineered mouse models of Parkinson's disease," Brain Research: Molecular Brain Research, Mar. 24, 2005, vol. 134, No. 1, pp. 67-75.
Eichler et al., "Hematopoietic Stem-Cell Gene Therapy for Cerebral Adrenoleukodystrophy," The New England Journal of Medicine, Oct. 26, 2017, vol. 377, No. 17, pp. 1630-1638.
Eichler et al., "Is Microglial Apoptosis an Early Pathogenic Change in Cerebral X-Linked Adrenoleukodystrophy?" Annals of Neurology, Jun. 2008, vol. 63, No. 6, pp. 729-742.
Elmore et al., "Colony-Stimulating Factor 1 Receptor Signaling Is Necessary for Microglia Viability, Unmasking a Microglia Progenitor Cell in the Adult Brain," Neuron, Apr. 16, 2014, vol. 82, pp. 380-397.
Engelen et al., "X-linked adrenoleukodystrophy (X-ALD): clinical presentation and guidelines for diagnosis, follow-up and management," Orphanet Journal of Rare Diseases, 2012, vol. 7, Article No. 51, pp. 1-14.
Escolar et al., "Transplantation of Umbilical-Cord Blood in Babies with Infantile Krabbe's Disease," The New England Journal of Medicine, May 19, 2005, vol. 352, No. 20, pp. 2069-2081.
Filippon et al., "Oxidative stress in patients with mucopolysaccharidosis type II before and during enzyme replacement therapy," Molecular Genetics and Metabolism, 2011, vol. 103, No. 2, pp. 121-127.
Futerman et al., "The Cell Biology of Lysosomal Storage Disorders," Nature Reviews: Molecular Cell Biology, Jul. 2004, vol. 5, pp. 554-565.
Gazit et al., "Fgd5 identifies hematopoietic stem cells in the murine bone marrow," The Journal of Experimental Medicine, 2014, vol. 211, No. 7, pp. 1315-1331.
Gentner et al., "Identification of Hematopoietic Stem Cell-Specific miRNAs Enables Gene Therapy of Globoid Cell Leukodystrophy," Science Translational Medicine, Nov. 17, 2010, vol. 2, No. 58, 58ra84, pp. 1-11, supplemental pp. 1-22.
Ginhoux et al., "Fate Mapping Analysis Reveals That Adult Microglia Derive from Primitive Macrophages," Science, Nov. 5, 2010, vol. 330, No. 6005, pp. 841-845.
Gosselin et al., "Environment Drives Selection and Function of Enhancers Controlling Tissue-Specific Macrophage Identities," Cell, Dec. 4, 2014, vol. 159, pp. 1327-1340.
Grommes et al., "Regulation of Microglial Phagocytosis and Inflammatory Gene Expression by Gas6 Acting on the Axl/Mer Family of Tyrosine Kinases," Journal of Neuroimmune Pharmacology, Jun. 2008, vol. 3, No. 2, pp. 130-140.
Hennecke et al., "RNA biomarkers of Parkinson's disease: developing tools for novel therapies," Biomarkers in Medicine, 2008, vol. 2, No. 1, pp. 41-53.
Hickman et al., "The Microglial Sensome Revealed by Direct RNA Sequencing," Nature Neuroscience, Dec. 2013, vol. 16, No. 12, pp. 1896-1905.
Hidalgo et al., "Expression of Metallothionein-I, -II, and -III in Alzheimer Disease and Animal Models of Neuroinflammation," Experimental Biology and Medicine, 2006, vol. 231, No. 9, pp. 1450-1458.
Hu et al., "Hematopoietic Stem Cell Transplantation and Lentiviral Vector-Based Gene Therapy for Krabbe's Disease: Present Convictions and Future Prospects," Journal of Neuroscience Research, 2016, vol. 94, pp. 1152-1168.
Arnal et al., "Clinical utility of copper, ceruloplasmin, and metallothionein plasma determinations in human neurodegenerative patients and their first-degree relatives," Brain Research, Mar. 10, 2010, vol. 1319, pp. 118-130.
Cartier et al., "Hematopoietic Stem Cell Transplantation and Hematopoietic Stem Cell Gene Therapy in X-Linked Adrenoleukodystrophy : X-Linked Adrenoleukodystrophy," Brain Pathology, Oct. 27, 2009, vol. 20, No. 4, pp. 857-862.
Extended European Search Report issued in corresponding European Patent Application No. 18741510.4, dated Nov. 18, 2020 (10 pages).
Cooper et al., "Immunobiological barriers to xenotransplantation," International Journal of Surgery, 2015, vol. 23, pp. 211-216.
Ikehara, Susumu, "Grand challenges in stem cell treatments," Frontiers in Cell and Developmental Biology, Oct. 2013, vol. 1, Article No. 2, pp. 1-2.
Liu et al., "The Immunogenicity and Immune Tolerance of Pluripotent Stem Cell Derivatives," Frontiers in Immunology, Jun. 2017, vol. 8, Article No. 645, pp. 1-6.
Paes et al., "Ten years of iPSC: clinical potential and advances in vitro hematopoietic differentiation," Cell Biology and Toxicology, 2017, vol. 33, pp. 233-250.
Sasaki et al., "The level of c-kit expression predicts the activity of murine hematopoietic stem cells," Cytometry Research, 2014, vol. 24, No. 1, pp. 19-23. [English Abstract].
Wang et al., "A Case of Allogenic Hematopoietic Stem Cell transplantation for Treatment of Mucopolysaccharidosis Type I," Journal of Clinical Hematology, Jan. 2008, vol. 21, No. 1, pp. 41-43. [English Summary].
Zhang et al. Scientific and Technical Documentation Press, 2012, p. 10. [English Summary].
Capotondo et al., "Intracerebroventricular delivery of hematopoietic progenitors results in rapid and robust engraftment of microglia-like cells," Science Advances, 2017, vol. 3, Article No. e170211, pp. 1-12.
De Munter et al., "Peroxisomal Disorders: A Review on Cerebellar Pathologies," Brain Pathology, 2015, vol. 25, pp. 663-678.
Watson et al., "Intrathecal administration of AAV vectors for the treatment of lysosomal storage in the brains of MPS I mice," Gene Therapy, 2006, vol. 13, pp. 917-925.
Examination Report dated Jan. 4, 2024 in corresponding European Patent Application No. 18741510.4 (11 pages).
Office Action dated Mar. 5, 2024 in corresponding Canadian Patent Application No. 3,050,690 (4 pages).

SEQUENCE LISTING

```
<160> NUMBER OF SEQ ID NOS: 25

<210> SEQ ID NO 1
<211> LENGTH: 745
<212> TYPE: PRT
<213> ORGANISM: Homo sapiens

<400> SEQUENCE: 1

Met Pro Val Leu Ser Arg Pro Arg Pro Trp Arg Gly Asn Thr Leu Lys
1               5                   10                  15

Arg Thr Ala Val Leu Leu Ala Leu Ala Ala Tyr Gly Ala His Lys Val
            20                  25                  30

Tyr Pro Leu Val Arg Gln Cys Leu Ala Pro Ala Arg Gly Leu Gln Ala
        35                  40                  45

Pro Ala Gly Glu Pro Thr Gln Glu Ala Ser Gly Val Ala Ala Ala Lys
    50                  55                  60

Ala Gly Met Asn Arg Val Phe Leu Gln Arg Leu Leu Trp Leu Leu Arg
65                  70                  75                  80

Leu Leu Phe Pro Arg Val Leu Cys Arg Glu Thr Gly Leu Leu Ala Leu
                85                  90                  95

His Ser Ala Ala Leu Val Ser Arg Thr Phe Leu Ser Val Tyr Val Ala
            100                 105                 110

Arg Leu Asp Gly Arg Leu Ala Arg Cys Ile Val Arg Lys Asp Pro Arg
        115                 120                 125
```

```
Ala Phe Gly Trp Gln Leu Leu Gln Trp Leu Leu Ile Ala Leu Pro Ala
    130                 135                 140

Thr Phe Val Asn Ser Ala Ile Arg Tyr Leu Glu Gly Gln Leu Ala Leu
145                 150                 155                 160

Ser Phe Arg Ser Arg Leu Val Ala His Ala Tyr Arg Leu Tyr Phe Ser
                165                 170                 175

Gln Gln Thr Tyr Tyr Arg Val Ser Asn Met Asp Gly Arg Leu Arg Asn
            180                 185                 190

Pro Asp Gln Ser Leu Thr Glu Asp Val Val Ala Phe Ala Ser Val
        195                 200                 205

Ala His Leu Tyr Ser Asn Leu Thr Lys Pro Leu Leu Asp Val Ala Val
    210                 215                 220

Thr Ser Tyr Thr Leu Leu Arg Ala Ala Arg Ser Arg Gly Ala Gly Thr
225                 230                 235                 240

Ala Trp Pro Ser Ala Ile Ala Gly Leu Val Val Phe Leu Thr Ala Asn
                245                 250                 255

Val Leu Arg Ala Phe Ser Pro Lys Phe Gly Glu Leu Val Ala Glu Glu
            260                 265                 270

Ala Arg Arg Lys Gly Glu Leu Arg Tyr Met His Ser Arg Val Val Ala
        275                 280                 285

Asn Ser Glu Glu Ile Ala Phe Tyr Gly Gly His Glu Val Glu Leu Ala
    290                 295                 300

Leu Leu Gln Arg Ser Tyr Gln Asp Leu Ala Ser Gln Ile Asn Leu Ile
305                 310                 315                 320

Leu Leu Glu Arg Leu Trp Tyr Val Met Leu Glu Gln Phe Leu Met Lys
                325                 330                 335

Tyr Val Trp Ser Ala Ser Gly Leu Leu Met Val Ala Val Pro Ile Ile
            340                 345                 350

Thr Ala Thr Gly Tyr Ser Glu Ser Asp Ala Glu Ala Val Lys Lys Ala
        355                 360                 365

Ala Leu Glu Lys Lys Glu Glu Leu Val Ser Glu Arg Thr Glu Ala
    370                 375                 380

Phe Thr Ile Ala Arg Asn Leu Leu Thr Ala Ala Asp Ala Ile Glu
385                 390                 395                 400

Arg Ile Met Ser Ser Tyr Lys Glu Val Thr Glu Leu Ala Gly Tyr Thr
                405                 410                 415

Ala Arg Val His Glu Met Phe Gln Val Phe Glu Asp Val Gln Arg Cys
            420                 425                 430

His Phe Lys Arg Pro Arg Glu Leu Glu Asp Ala Gln Ala Gly Ser Gly
        435                 440                 445

Thr Ile Gly Arg Ser Gly Val Arg Val Glu Gly Pro Leu Lys Ile Arg
    450                 455                 460

Gly Gln Val Val Asp Val Glu Gln Gly Ile Ile Cys Glu Asn Ile Pro
465                 470                 475                 480

Ile Val Thr Pro Ser Gly Glu Val Val Ala Ser Leu Asn Ile Arg
                485                 490                 495

Val Glu Glu Gly Met His Leu Leu Ile Thr Gly Pro Asn Gly Cys Gly
            500                 505                 510

Lys Ser Ser Leu Phe Arg Ile Leu Gly Gly Leu Trp Pro Thr Tyr Gly
        515                 520                 525

Gly Val Leu Tyr Lys Pro Pro Gln Arg Met Phe Tyr Ile Pro Gln
    530                 535                 540

Arg Pro Tyr Met Ser Val Gly Ser Leu Arg Asp Gln Val Ile Tyr Pro
```

```
545                 550                 555                 560
Asp Ser Val Glu Asp Met Gln Arg Lys Gly Tyr Ser Glu Gln Asp Leu
                565                 570                 575
Glu Ala Ile Leu Asp Val Val His Leu His Ile Leu Gln Arg Glu
            580                 585                 590
Gly Gly Trp Glu Ala Met Cys Asp Trp Lys Asp Val Leu Ser Gly Gly
        595                 600                 605
Glu Lys Gln Arg Ile Gly Met Ala Arg Met Phe Tyr His Arg Pro Lys
    610                 615                 620
Tyr Ala Leu Leu Asp Glu Cys Thr Ser Ala Val Ser Ile Asp Val Glu
625                 630                 635                 640
Gly Lys Ile Phe Gln Ala Ala Lys Asp Ala Gly Ile Ala Leu Leu Ser
                645                 650                 655
Ile Thr His Arg Pro Ser Leu Trp Lys Tyr His Thr His Leu Leu Gln
            660                 665                 670
Phe Asp Gly Glu Gly Gly Trp Lys Phe Glu Lys Leu Asp Ser Ala Ala
        675                 680                 685
Arg Leu Ser Leu Thr Glu Glu Lys Gln Arg Leu Glu Gln Gln Leu Ala
    690                 695                 700
Gly Ile Pro Lys Met Gln Arg Arg Leu Gln Glu Leu Cys Gln Ile Leu
705                 710                 715                 720
Gly Glu Ala Val Ala Pro Ala His Val Pro Ala Pro Ser Pro Gln Gly
                725                 730                 735
Pro Gly Gly Leu Gln Gly Ala Ser Thr
                740                 745

<210> SEQ ID NO 2
<211> LENGTH: 3697
<212> TYPE: DNA
<213> ORGANISM: Homo sapiens

<400> SEQUENCE: 2
gccaggctgc ggagcggacg gacgcgcctg gtgccccggg gaggggcgcc accgggggag      60
gaggaggagg agaaggtgga gaggaagaga cgcccctct gcccgagacc tctcaaggcc     120
ctgacctcag gggccagggc actgacagga caggagagcc aagttcctcc acttgggctg     180
cccgaagagg ccgcgaccct ggagggccct gagcccaccg caccagggc cccagcacca     240 ccccggggc ctaaagcgac agtctcaggg gccatcgcaa ggtttccagt tgcctagaca     300
acaggcccag ggtcagagca acaatccttc cagccacctg cctcaactgc tgccccaggc     360
accagcccca gtccctacgc ggcagccagc ccaggtgaca tgccggtgct ctccaggccc     420
cggccctggc gggggaacac gctgaagcgc acggccgtgc cctggcccct cgcggcctat     480
ggagcccaca agtctaccc cttggtgcgc cagtgcctgg ccccggccag gggtcttcag     540
gcgcccgccg gggagcccac gcaggaggcc tccggggtcg cggcggccaa agctggcatg     600
aaccgggtat tcctgcagcg gctcctgtgg ctcctgcggc tgctgttccc ccgggtcctg     660
tgccgggaga cggggctgct ggccctgcac tcggccgcct ggtgagccg accttcctg     720 tcggtgtatg tggcccgcct ggacggaagg ctggcccgct gcatcgtccg caaggacccg     780
cgggcttttg gctggcagct gctgcagtgg ctcctcatcg ccctccctgc taccttcgtc     840
aacagtgcca tccgttacct ggagggccaa ctggccctgt cgttccgcag ccgtctggtg     900
gcccacgcct accgctctca cttctcccag cagacctact accgggtcag caacatggac     960
gggcggcttc gcaaccctga ccagtctctg acggaggacg tggtggcctt tgcggcctct    1020
```

```
gtggcccacc tctactccaa cctgaccaag ccactcctgg acgtggctgt gacttcctac    1080
accctgcttc gggcggcccg ctcccgtgga gccggcacag cctggccctc ggccatcgcc    1140
ggcctcgtgg tgttcctcac ggccaacgtg ctgcgggcct tctcgcccaa gttcggggag    1200
ctggtggcag aggaggcgcg gcggaagggg gagctgcgct acatgcactc gcgtgtggtg    1260
gccaactcgg aggagatcgc cttctatggg ggccatgagg tggagctggc cctgctacag    1320
cgctcctacc aggacctggc ctcgcagatc aacctcatcc ttctggaacg cctgtggtat    1380
gttatgctgg agcagttcct catgaagtat gtgtggagcg cctcgggcct gctcatggtg    1440
gctgtcccca tcatcactgc cactggctac tcagagtcag atgcagaggc cgtgaagaag    1500
gcagccttgg aaaagaagga ggaggagctg gtgagcgagc gcacagaagc cttcactatt    1560
gcccgcaacc tcctgacagc ggctgcagat gccattgagc ggatcatgtc gtcgtacaag    1620
gaggtgacgg agctggctgg ctacacagcc cgggtgcacg agatgttcca ggtatttgaa    1680
gatgttcagc gctgtcactt caagaggccc agggagctag aggacgctca ggcggggtct    1740
gggaccatag gccggtctgg tgtccgtgtg gagggccccc tgaagatccg aggccaggtg    1800
gtggatgtga acaggggat catctgcgag aacatcccca tcgtcacgcc ctcaggagag    1860
gtggtggtgg ccagcctcaa catcagggtg gaggaaggca tgcatctgct catcacaggc    1920
cccaatggct gcggcaagag ctccctgttc cggatcctgg tgggctctg gcccacgtac    1980 ggtggtgtgc tctacaagcc cccaccccag cgcatgttct catcccgca gaggccctac    2040 atgtctgtgg gctccctgcg tgaccaggtg atctacccgg actcagtgga ggacatgcaa    2100
aggaagggct actcggagca ggacctggaa gccatcctgg acgtcgtgca cctgcaccac    2160
atcctgcagc gggagggagg ttgggaggct atgtgtgact ggaaggacgt cctgtcgggt    2220
ggcgagaagc agagaatcgg catggcccgc atgttctacc acaggcccaa gtacgccctc    2280
ctggatgaat gcaccagcgc cgtgagcatc gacgtggaag gcaagatctt ccaggcggcc    2340
aaggacgcgg gcattgccct gctctccatc acccaccggc cctccctgtg gaaataccac    2400
acacacttgc tacagttcga tggggagggc ggctggaagt tcgagaagct ggactcagct    2460
gcccgcctga gctgacggga ggagaagcag cggctggagc agcagctggc gggcattccc    2520
aagatgcagc ggcgcctcca ggagctctgc cagatcctgg gcgaggccgt ggccccagcg    2580
catgtgccgg cacctagccc gcaaggccct ggtggcctcc agggtgcctc cacctgacac    2640
aaccgtcccc ggcccctgcc ccgcccccaa gctcggatca catgaaggag acagcagcac    2700
ccacccatgc acgcaccccg cccctgcatg cctggcccct cctcctagaa aacccttccc    2760
gccctcggga aagtagatgt ggagggtggc gccctgcgta accctcgccc tgtccctccc    2820
actcctgggg ggcgctgttc cacagtgact gggccctgtc cagggcagtg agtcctctac    2880
tttgctccgt ggaggaagct ggggtacaag gggcccagtg ctggccacac agcagcgcag    2940
ccgagcccca ggagccgtc aggccacagc ccctggcact gcaggtggcc tccctccaga    3000
gactcgagtc cccatgattc cctcctcgtc agtctctcaa agaccccatg gtccatcccc    3060
tgagggtggt cagccaaggc tcccgttccg tgggatgcca taaaagccgc ccagtgggac    3120
ccacagtcac acagagcgcc tcacctgcat cctctccccc acaagagccc caaagatccc    3180
acgggagagg ggagagggac gcacagcact gcctgccaag cgagaatgca ggccccgccc    3240
cctcggcccc tcaccacctc tttctacagc ctaatttatt ggattcccta ttcgtagcca    3300
tctccgtggc caatgtgact accgtgccag cagcgggggc ggcccagcct ctgagtcccg    3360
```

```
tggggccccg gctcccaccg gtgccaaacc cagcccctgc ggccgtcacc ccgccagcct  3420
acactgccag ccgccaccgg ggcacacggg cctctgcttg ccagccagga gtgcggacac  3480
catgttccca gctcagtgcc aaagaggggt caccaggggg agctgtctgc ggagccagcg  3540
cctgcccgag agagacccca ccgccaccgt gtgcctttcc cgggccctca gccctcgggc  3600
cgggcaccac ccccagtccc cccagtaaaa gcctccactg gcaaatgcag tccttcctcc  3660
ctgcaaaaaa aaaaaaaaaa aaaaaaaaaa aaaaaa                             3697
```

<210> SEQ ID NO 3
<211> LENGTH: 61
<212> TYPE: PRT
<213> ORGANISM: Homo sapiens

<400> SEQUENCE: 3

```
Met Asp Pro Asn Cys Ser Cys Ala Thr Gly Gly Ser Cys Thr Cys Thr
1               5                   10                  15

Gly Ser Cys Lys Cys Lys Glu Cys Lys Cys Thr Ser Cys Lys Lys Ser
            20                  25                  30

Cys Cys Ser Cys Cys Pro Met Ser Cys Ala Lys Cys Ala Gln Gly Cys
        35                  40                  45

Ile Cys Lys Gly Ala Ser Glu Lys Cys Ser Cys Cys Ala
    50                  55                  60
```

<210> SEQ ID NO 4
<211> LENGTH: 61
<212> TYPE: PRT
<213> ORGANISM: Homo sapiens

<400> SEQUENCE: 4

```
Met Asp Pro Asn Cys Ser Cys Thr Thr Gly Gly Ser Cys Ala Cys Ala
1               5                   10                  15

Gly Ser Cys Lys Cys Lys Glu Cys Lys Cys Thr Ser Cys Lys Lys Cys
            20                  25                  30

Cys Cys Ser Cys Cys Pro Val Gly Cys Ala Lys Cys Ala Gln Gly Cys
        35                  40                  45

Val Cys Lys Gly Ser Ser Glu Lys Cys Arg Cys Cys Ala
    50                  55                  60
```

<210> SEQ ID NO 5
<211> LENGTH: 61
<212> TYPE: PRT
<213> ORGANISM: Homo sapiens

<400> SEQUENCE: 5

```
Met Asp Pro Asn Cys Ser Cys Ala Thr Gly Gly Ser Cys Thr Cys Ala
1               5                   10                  15

Gly Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala Gln Gly Cys
        35                  40                  45

Val Cys Lys Gly Ala Ser Glu Lys Cys Ser Cys Cys Ala
    50                  55                  60
```

<210> SEQ ID NO 6
<211> LENGTH: 61
<212> TYPE: PRT
<213> ORGANISM: Homo sapiens

<400> SEQUENCE: 6

Met Asp Pro Asn Cys Ser Cys Ala Ala Gly Val Ser Cys Thr Cys Ala
1               5                   10                  15

Gly Ser Cys Lys Cys Lys Glu Cys Lys Cys Thr Ser Cys Lys Lys Ser
            20                  25                  30

Cys Cys Ser Cys Cys Pro Val Gly Cys Ser Lys Cys Ala Gln Gly Cys
            35                  40                  45

Val Cys Lys Gly Ala Ser Glu Lys Cys Ser Cys Asp
    50                  55                  60

<210> SEQ ID NO 7
<211> LENGTH: 61
<212> TYPE: PRT
<213> ORGANISM: Homo sapiens

<400> SEQUENCE: 7

Met Asp Pro Asn Cys Ser Cys Ala Ala Gly Val Ser Cys Thr Cys Ala
1               5                   10                  15

Ser Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala Gln Gly Cys
            35                  40                  45

Ile Cys Lys Gly Ala Ser Glu Lys Cys Ser Cys Ala
    50                  55                  60

<210> SEQ ID NO 8
<211> LENGTH: 61
<212> TYPE: PRT
<213> ORGANISM: Homo sapiens

<400> SEQUENCE: 8

Met Asp Pro Asn Cys Ser Cys Glu Ala Gly Gly Ser Cys Ala Cys Ala
1               5                   10                  15

Gly Ser Cys Lys Cys Lys Lys Cys Lys Cys Thr Ser Cys Lys Lys Ser
            20                  25                  30

Cys Cys Ser Cys Cys Pro Leu Gly Cys Ala Lys Cys Ala Gln Gly Cys
            35                  40                  45

Ile Cys Lys Gly Ala Ser Glu Lys Cys Ser Cys Ala
    50                  55                  60

<210> SEQ ID NO 9
<211> LENGTH: 61
<212> TYPE: PRT
<213> ORGANISM: Homo sapiens

<400> SEQUENCE: 9

Met Asp Pro Asn Cys Ser Cys Thr Thr Gly Val Ser Cys Ala Cys Thr
1               5                   10                  15

Gly Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala His Gly Cys
            35                  40                  45

Val Cys Lys Gly Thr Leu Glu Asn Cys Ser Cys Ala
    50                  55                  60

<210> SEQ ID NO 10
<211> LENGTH: 61
<212> TYPE: PRT
<213> ORGANISM: Homo sapiens

```
<400> SEQUENCE: 10

Met Asp Pro Asn Cys Ser Cys Ser Pro Val Gly Ser Cys Ala Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ala Lys Cys Ala Gln Gly Cys
            35                  40                  45

Ile Cys Lys Gly Thr Ser Asp Lys Cys Ser Cys Ala
50                  55                  60

<210> SEQ ID NO 11
<211> LENGTH: 61
<212> TYPE: PRT
<213> ORGANISM: Homo sapiens

<400> SEQUENCE: 11

Met Asp Pro Asn Cys Ser Cys Ala Ala Gly Asp Ser Cys Thr Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ala Lys Cys Ala Gln Gly Cys
            35                  40                  45

Ile Cys Lys Gly Ala Ser Asp Lys Cys Ser Cys Ala
50                  55                  60

<210> SEQ ID NO 12
<211> LENGTH: 68
<212> TYPE: PRT
<213> ORGANISM: Homo sapiens

<400> SEQUENCE: 12

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
                20                  25                  30

Ser Cys Cys Ser Cys Cys Pro Ala Glu Cys Glu Lys Cys Ala Lys Asp
            35                  40                  45

Cys Val Cys Lys Gly Gly Glu Ala Ala Glu Ala Glu Ala Glu Lys Cys
        50                  55                  60

Ser Cys Cys Gln
65

<210> SEQ ID NO 13
<211> LENGTH: 62
<212> TYPE: PRT
<213> ORGANISM: Homo sapiens

<400> SEQUENCE: 13

Met Asp Pro Arg Glu Cys Val Cys Met Ser Gly Gly Ile Cys Met Cys
1               5                   10                  15

Gly Asp Asn Cys Lys Cys Thr Thr Cys Asn Cys Lys Thr Cys Arg Lys
                20                  25                  30

Ser Cys Cys Pro Cys Cys Pro Pro Gly Cys Ala Lys Cys Ala Arg Gly
            35                  40                  45

Cys Ile Cys Lys Gly Gly Ser Asp Lys Cys Ser Cys Cys Pro
    50                  55                  60

<210> SEQ ID NO 14
```

<211> LENGTH: 468
<212> TYPE: DNA
<213> ORGANISM: Homo sapiens

<400> SEQUENCE: 14

```
accaagcctt ccacgtgcgc cttatagcct ctcaacttct tgcttgggat ctccaacctc    60
accgcggctc gaaatggacc ccaactgctc ctgcgccact ggtggctcct gcacctgcac   120
tggctcctgc aaatgcaaag agtgcaaatg cacctcctgc aagaagagct gctgctcctg   180
ctgccccatg agctgtgcca agtgtgccca gggctgcatc tgcaaggggg catcagagaa   240
gtgcagctgc tgtgcctgat gtccggacag ccctgctcga agatatagaa agagtgacct   300
gcacaaactt ggaattttttt ttccatacaa ccctgaccca tttactgtat tttttttaat   360
gaaatatgtg aatgataata aagttgctg acttaaaaaa aaaaaaaaaa aaaaaaaaaa   420
aaaaaaaaaa aaaaaaaaaa aaaaaaaaaa aaaaaaaaaa aaaaaaa                468
```

<210> SEQ ID NO 15
<211> LENGTH: 519
<212> TYPE: DNA
<213> ORGANISM: Homo sapiens

<400> SEQUENCE: 15

```
aggaacgcgg gcggtgcgga ctcagcgggc cgggtgcagg cgcggagctg ggcctctgcg    60
cccggcccga cctccgtcta taaatagagc agccagttgc agggctccat tctgctttcc   120
aactgcctga ctgcttgttc gtctcactgg tgtgagctcc agcatcccct ttgctcgaaa   180
tggaccccaa ctgctcttgc gccactggtg gctcctgcac gtgcgccggc tcctgcaagt   240
gcaaagagtg caaatgcacc tcctgcaaga agagctgctg ttcctgctgc cccgtgggct   300
gtgccaagtg tgcccagggc tgcgtctgca aggggcatc ggagaagtgc agctgctgtg   360
cctgatgtgg gaacagctct tctcccagat gtaaatagaa caacctgcac aacctggatt   420
tttttaaaaa tacaacactg agccatttgc tgcatttctt tttatactaa atatgtgact   480
gacaataaaa acaatttgta ctttaaaaaa aaaaaaaaa                          519
```

<210> SEQ ID NO 16
<211> LENGTH: 456
<212> TYPE: DNA
<213> ORGANISM: Homo sapiens

<400> SEQUENCE: 16

```
gcccctccc ctgactatca aagcagcggc cggctgttgg ggtccaccac gccttccacc    60
tgccccactg cttcttcgct tctctcttgg aaagtccagt ctctcctcgg cttgcaatgg   120
accccaactg ctcctgcgcc gctggtgtct cctgcacctg cgctggttcc tgcaagtgca   180
aagagtgcaa atgcacctcc tgcaagaaga gctgctgctc ctgctgcccc gtgggctgta   240
gcaagtgtgc ccagggctgt gtttgcaaag gggcgtcaga aagtgcagc tgctgcgact   300
gatgccagga caaccttctct cccagatgta aacagagaga catgtacaaa cctggatttt   360
tttttatac caccttgacc catttgctac attcctttc ctgtgaaata tgtgagtgat   420
aattaaacac tttagacctg aaaaaaaaaa aaaaaa                             456
```

<210> SEQ ID NO 17
<211> LENGTH: 420
<212> TYPE: DNA
<213> ORGANISM: Homo sapiens

<400> SEQUENCE: 17

```
actccgcctt ccacgtgcac ccactgcctc ttcccttctc gcttgggaac tctagtctcg    60 cctcggggttg caatggaccc caactgctcc tgtgccgctg gtgtctcctg cacctgcgcc   120
agctcctgca agtgcaaaga gtgcaaatgc acctcctgca agaagagctg ctgctcctgc   180
tgccctgtgg gctgtgccaa gtgtgcccag ggctgcatct gcaaaggggc atcggagaag   240
tgcagctgct gcgcctgatg tcgggacagc cctgctccca agtacaaata gagtgacccg   300
taaaatccag gattttttgt ttttgctac aatcttgacc cctttgctac attccttttt    360
ttctgtgaaa tatgtgaata ataattaaac acttagactt gaaaaaaaaa aaaaaaaaa    420
```

<210> SEQ ID NO 18
<211> LENGTH: 397
<212> TYPE: DNA
<213> ORGANISM: Homo sapiens

<400> SEQUENCE: 18

```
accacgccct ccacgtgttc cactgcctct tctcttctcg cttgggaact ccagtctcac    60
ctcggcttgc aatggacccc aactgctcct gcgaggctgg tggctcctgc gcctgcgccg   120
gctcctgcaa gtgcaaaaag tgcaaatgca cctcctgcaa gaagagctgc tgctcctgtt   180
gccccctggg ctgtgccaag tgtgcccagg gctgcatctg caaggggcg tcagagaagt    240 gcagctgctg tgcctgatgt cgggacagcc ctgctgtcag atgaaaacag aatgacacgt   300
aaaatccagg attttttttt tctacaactc cgactcattt gctacattcc ttttttctg    360 tgaaatatgt gaataataat taaacactta gacttga                            397
```

<210> SEQ ID NO 19
<211> LENGTH: 372
<212> TYPE: DNA
<213> ORGANISM: Homo sapiens

<400> SEQUENCE: 19

```
tccaccacgc ctcccacctg ccccactgct tcttctcctc tcccttagga actctagctt    60
cacctcgctt cgtaatggac cccaattgct cctgctccac tactcctgca aatgcagaga   120
gtgcaaatgc acctcctgca agacgagctg ctgctcctgc tgccccgtgg gctgtgccaa   180
gtgtgcccag ggatgtgttt gcaaagggac actgacaagt gcagctgctg ctcctgatgt   240
agggaaagct gtgttcccag aagtagaaag tgtacaaacc tggaattgtt ttccatacaa   300
ccctgaccca ttagtacatt tgggtttcta aaaataaaat atgttaatga taataaaagt   360
tgactttatt ct                                                       372
```

<210> SEQ ID NO 20
<211> LENGTH: 443
<212> TYPE: DNA
<213> ORGANISM: Homo sapiens

<400> SEQUENCE: 20

```
gtcccatctc cgcctgcaaa aggagcagct ggctccaggc tccaacgtgc cttccagctg    60
cctgactgcc tcttcgcctc tcccgtcatt tcttggctcg aaatggaccc caactgctcc   120
tgcgccactg ggggctcctg ctcctgtgcc agctcctgca agtgcaaaga gtgcaaatga   180
acctcctgca agaagagctg ctgctcctgc tgccccatgg gctgtgccaa gtgtgcccag   240
ggctgcgtct gcaagggggc gtcggagaag tgcagctgct gtgcctgatg tggggacagc   300
cctgctccca gatgtaaaca gagcaacctg cacaaacctg gattttttttt tcatacaacc  360
```

```
ctgagcattt gctacattcc tttttctatt aaatatgtaa acgacaataa aacagttttg    420
acttgaaaaa aaaaaaaaaa aaa                                            443

<210> SEQ ID NO 21
<211> LENGTH: 464
<212> TYPE: DNA
<213> ORGANISM: Homo sapiens

<400> SEQUENCE: 21
ccctgagtag aaaagcagcc gcaggctgtg gcgctccacc acgccgtccg ggtgggccta     60
gcagtcgctc catttatcgc ttgagatctc cagccttacc gcggctcgaa atggacccca   120
actgctcctg caccactggt gtctcctgcg cctgcaccgg ctcctgcaag tgcaaagagt   180
gcaaatgcac ctcctgcaag aagagctgct gtcctgctg ccccgtgggc tgtgccaagt    240
gtgcccacgg ctgtgtctgc aaagggacgt tggagaactg cagctgctgt gcctgatgtg   300
ggaacagctc ttctcccaga tgttaataga acaagctgca caacctggat ttttttttcaa  360 tacgatactg agccatttgc tgcatttctt tttatattaa atatgtgagt gacaataaaa   420
caattttgac ttgaatctta aaaaaaaaaa aaaaaaaaaa aaaa                     464

<210> SEQ ID NO 22
<211> LENGTH: 468
<212> TYPE: DNA
<213> ORGANISM: Homo sapiens

<400> SEQUENCE: 22
accacgcttt tcatctgtcc cgctgcgtgt tttcctcttg atcgggaact cctgcttctc     60
cttgcctcga aatggacccc aactgctcct gctcgcctgt tggctcctgt gcctgtgccg   120
gctcctgcaa atgcaaagag tgcaaatgca cctcctgcaa gaagagctgc tgctcctgct   180
gccctgtggg ctgtgccaag tgtgcccagg gctgcatctg caaagggacg tcagacaagt   240
gcagctgctg tgcctgatgc caggacagct gtgctctcag atgtaaatag agcaacctat   300
ataaacctgg atttttttttt tttttttttt tgtacaaccc tgacccgttt gctacatctt   360
tttttctatg aaatatgtga atggcaataa attcatctag actaaaaaaa aaaaaaaaaa   420
aaaaaaaaaa aaaaaaaaaa aaaaaaaaaa aaaaaaaaaa aaaaaaaa                468

<210> SEQ ID NO 23
<211> LENGTH: 466
<212> TYPE: DNA
<213> ORGANISM: Homo sapiens

<400> SEQUENCE: 23
cttgccgcgc tgcactccac cacgcctcct ccaagtccca gcgaaccgc gtgcaacctg      60 tcccgactct agccgcctct tcagctcgcc atggatccca actgctcctg cgccgccggt   120
gactcctgca cctgcgccgg ctcctgcaaa tgcaaagagt gcaaatgcac ctcctgcaag   180
aaaagctgct gctcctgctg ccctgtgggc tgtgccaagt gtgcccaggg ctgcatctgc   240
aaaggggcgt cggacaagtg cagctgctgc gcctgatgct gggacagccc cgctcccaga   300
tgtaaagaac gcgacttcca caaacctgga ttttttatgt acaaccctga ccgtgaccgt   360
ttgctatatt ccttttttcta tgaaataatg tgaatgataa taaaacagct ttgacttgaa   420
aaaaaaaaaa aaaaaaaaaa aaaaaaaaaa aaaaaaaaaa aaaaaa                  466

<210> SEQ ID NO 24
<211> LENGTH: 599
```

```
<212> TYPE: DNA
<213> ORGANISM: Homo sapiens

<400> SEQUENCE: 24
cccggcagtg cacacacacg gcagggggcgg gcgacagatg cagtgcgtgc gccggagccc      60
aagcgcacaa acggaaagag cgggcgcggt gcgcaggggc gggcgcccag cgggcttggc     120
atgcgcgccc ccgcccgagg ctataaaagc atcgccacct gctgccacta gccaagccgc     180
gcgtccagtt gcttggagaa gcccgttcac cgcctccagc tgctgctctc ctcgacatgg     240
accctgagac ctgcccctgc ccttctggtg gctcctgcac ctgcgcggac tcctgcaagt     300
gcgagggatg caaatgcacc tcctgcaaga agagctgctg ctcctgctgc cctgcggagt     360
gtgagaagtg tgccaaggac tgtgtgtgca aaggcggaga ggcagctgag gcagaagcag     420
agaagtgcag ctgctgccag tgagaaggca cccctccgtg tggagcacgt ggagatagtg     480
ccaggtggct cagtgccacc tatgcctgtg gtgaagtgtg gctggtgtcc ccttcccctg     540
ctgaccttgg aggaatgaca ataaatccca tgaacagcat gaaaaaaaaa aaaaaaaaa     599

<210> SEQ ID NO 25
<211> LENGTH: 294
<212> TYPE: DNA
<213> ORGANISM: Homo sapiens

<400> SEQUENCE: 25
atggggagcc tctggctgct gctcactcag cctcccttcc ccagccgtga cagcactgga      60
gcctttcgga cacctggacc atggaccccca gggaatgtgt ctgcatgtct ggaggaatct     120
gcatgtgtgg agacaactgc aaatgcacaa cctgcaactg taaaacatgt cggaagagct     180
gctgtccctg ctgcccccg ggctgtgcca aatgtgcccg gggctgcatc tgcaaaggag     240
gctcagacaa gtgcagctgc tgcccatgaa agccatccat cgtgcccacc cctt          294
```

COMPOSITIONS AND METHODS FOR DIAGNOSING AND TREATING PEROXISOMAL DISEASES

CROSS-REFERENCE TO RELATED APPLICATIONS

This application is the U.S. National Phase application, pursuant to 35 U.S.C. § 371, of PCT International Application Serial No.: PCT/US2018/013908, filed Jan. 16, 2018, designating the United States and published in English, which claims priority to and the benefit of U.S. Provisional Application No. 62/447,346, filed Jan. 17, 2017, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 17, 2020, is named 167705_010802_US_SL.txt and is 26,273 bytes in size.

BACKGROUND OF THE INVENTION

Peroxisome diseases with central nervous system (CNS) involvement lack an effective and curative treatment and patients eventually succumb to their devastating disease. Frequently, disease onset occurs in very early infancy and is characterized by subtle manifestations, leading to diagnosis in clearly symptomatic if not advanced stage. In some cases, peroxisome diseases are characterized by a rapid early disease progression, particularly in early onset variants.

At present, methods of diagnosis and monitoring of peroxisome disease are limited. For example, therapeutic intervention is indicated in patients with cerebral X-ALD (cALD) by detection of CNS lesions using contrast enhancement with brain magnetic resonance imaging (MRI). Accordingly, novel compositions and methods of identifying and treating patients with peroxisomal diseases are urgently required.

SUMMARY OF THE INVENTION

As described below, the present invention features compositions and methods for the treatment or prevention of a peroxisomal disease (e.g., neonatal adrenoleukodystrophy and Zellweger syndrome). In some embodiments, the method involves identifying peroxisomal disease patients with active CNS disease and monitoring the course of the disease. The invention provides compositions and methods for measuring one or more metallothioneins, which, when elevated (e.g., in cerebrospinal fluid and peripheral blood cells), have been found to indicate high risk of developing severe and rapidly progressive brain damage in subjects having peroxisomal disease. Accordingly, this allows for intense clinical monitoring and/or therapuetic treatment selection for subjects at high risk.

In one aspect, the invention provides a method of treating a peroxisomal disease in a pre-selected subject, involving administering a peroxisomal disease treatment to the subject, where the subject is pre-selected by detecting an increase in the level of a metallothionein (MT) polynucleotide or polypeptide in a sample of the subject relative to a reference.

In one aspect, the invention provides a method of identifying a subject having or being at increased risk of developing a peroxisomal disease, involving detecting an increase in the level of a metallothionein (MT) polynucleotide or polypeptide in a sample of the subject relative to a reference, thereby identifying said subject as having or being at increased risk of developing a peroxisomal disease.

In various embodiments of any aspect delineated herein, the metallothionein (MT) polynucleotide or polypeptide is detected at the transcript (mRNA) or protein level in a sample of the subject. In various embodiments, the sample comprises cerebrospinal fluid, peripheral blood, and derivatives thereof. In particular embodiments, the MT polypeptide levels are determined by Western blot, tandem mass spectrometry, or enzyme linked immunosorbent assay (ELISA).

In various embodiments of any aspect delineated herein, the peroxisomal disease is adrenoleukodystrophy, neonatal adrenoleukodystrophy, adrenomyeloneuropathy, or Zellweger syndrome. In various embodiments, the peroxisomal disease comprises cerebral involvement.

In various embodiments of any aspect delineated herein, the metallothionein is one or more of metallothionein-1A (MT1A), metallothionein-1B (MT1B), metallothionein-1E (MT1E), metallothionein-1F (MT1F), metallothionein-1G (MT1G), metallothionein-1H (MT1H), metallothionein-1I pseudogene (MT1Ip or MTE), metallothionein-1L (LT1L or MT1R), metallothionem-1M (MT1M or MT1K), metallothionein-1X (MT1X), metallothionein-2 (MT2), metallothionein-2A (MT2A), metallothionein-3 (MT3), and metallothionein-4 (MT4).

In various embodiments of any aspect delineated herein, the peroxisomal disease treatment involves administering a Hematopoietic Stem Cell (HSC), lentiviral vector, or adenoassociated vector to the subject. In various embodiments of any aspect delineated herein, the peroxisomal disease treatment involves increasing or restoring ABCD1 gene function or ALDP polypeptide function (e.g., expression of ALDP polypeptide). In various embodiments, the adenoassociated vectors are delivered either intra-thecally or intra-venously.

In various embodiments of any aspect delineated herein, the method involves delivering Hematopoietic Stem Cells (HSC) to a subject, including by administering the HSC by Intra-cerebral Ventricular Injection (ICV) and/or in combination with ablative conditioning In various embodiments of any aspect delineated herein, the method involves treating a subject having or being at increased risk of developing a peroxisomal disease.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "adrenoleukodystrophy protein (ALDP) polypeptide" is meant a a polypeptide or fragment thereof having at least about 85% or greater seqeunce identity to the amino acid sequence provided at NCBI Accession No. NP_000024 and having peroxisomal fatty acid import activity. An exemplary human ALDP amino acid sequence is provided below (SEQ ID NO: 1):

```
  1  mpvlsrprpw rgntlkrtav llalaaygah kvyplvrqcl aparglqapa geptqeasgv
 61  aaakagmnrv flqrllwllr llfprvlcre tgllalhsaa lvsrtflsvy varldgrlar
121  civrkdpraf gwqllqwlli alpatfvnsa irylegqlal sfrsrlvaha yrlyfsqqty
181  yrvsnmdgrl rnpdqslted vvafaasvah lysnltkpll dvavtsytll raarsrgagt
241  awpsaiaglv vfltanvlra fspkfgelva eearrkgelr ymhsrvvans eeiafygghe
301  velallqrsy qdlasqinli llerlwyvml eqflmkyvws asgllmvavp iitatgyses
361  daeavkkaal ekkeeelvse rteaftiarn lltaaadaie rimssykevt elagytarvh
421  emfqvfedvq rchfkrprel edaqagsgti grsgvrvegp lkirgqvvdv eqgiicenip
481  ivtpsgevvv aslnirveeg mhllitgpng cgksslfril gglwptyggv lykpppqrmf
541  yipqrpymsv gslrdqviyp dsvedmqrkg yseqdleail dvvhlhhilq reggweamcd
601  wkdvlsggek qrigmarmfy hrpkyallde ctsavsidve gkifqaakda giallsithr
661  pslwkyhthl lqfdgeggwk fekldsaarl slteekqrle qqlagipkmq rrlqelcqil
721  geavapahvp apspqgpggl qgast
```

By "ABCD1 polynucleottide" is meant a polynucleottide having at least about 85% or greater sequence identity to the nucleic acid sequence provided at NCBI Accession No. NM_000033 (SEQ ID NO: 2), which is provided below, and encoding an ALDP polypeptide.

```
   1  gccaggctgc ggagcggacg gacgcgcctg gtgccccggg gagggcgcc accggggag
  61  gaggaggagg agaaggtgga gaggaagaga cgcccctct gcccgagacc tctcaaggcc
 121  ctgacctcag gggccagggc actgacagga caggagagcc aagttcctcc acttgggctg
 181  cccgaagagg ccgcgaccct ggaggcccct gagcccaccg caccagggc cccagcacca
 241  ccccgggggc ctaaagcgac agtctcaggg gccatcgcaa ggtttccagt tgcctagaca
 301  acaggcccag ggtcagagca acaatccttc cagccacctg cctcaactgc tgccccaggc
 361  accagcccca gtccctacgc ggcagccagc ccaggtgaca tgccggtgct ctccaggccc
 421  cggccctggc ggggaacac gctgaagcgc acggccgtgc tcctggccct cgcggcctat
 481  ggagcccaca agtctacccc cttggtgcgc cagtgcctgg ccccggccag gggtcttcag
 541  gcgcccgccg ggagcccac gcaggaggcc tccggggtcg cggcggccaa agctggcatg
 601  aaccgggtat tcctgcagcg gctcctgtgg ctcctgcggc tgctgttccc ccgggtcctg
 661  tgccgggaga cggggctgct ggccctgcac tcggccgcct tggtgagccg caccttcctg
 721  tcggtgtatg tggcccgcct ggacggaagg ctggcccgct gcatcgtccg caaggacccg
 781  cgggcttttg gctggcagct gctgcagtgg ctcctcatcg ccctccctgc taccttcgtc
 841  aacagtgcca tccgttacct ggagggccaa ctggccctgt cgttccgcag ccgtctggtg
 901  gcccacgcct accgcctcta cttctcccag cagacctact accgggtcag caacatggac
 961  gggcggcttc gcaaccctga ccagtctctg acggaggacg tggtggcctt tgcggcctct
1021  gtggcccacc tctactccaa cctgaccaag ccactcctgg acgtggctgt gacttcctac
1081  accctgcttc gggcggcccg ctcccgtgga gccggcacag cctggccctc ggccatcgcc
1141  ggcctcgtgg tgttcctcac ggccaacgtg ctgcgggcct tctcgcccaa gttcggggag
```

-continued

```
1201 ctggtggcag aggaggcgcg gcggaagggg gagctgcgct acatgcactc gcgtgtggtg
1261 gccaactcgg aggagatcgc cttctatggg ggccatgagg tggagctggc cctgctacag
1321 cgctcctacc aggacctggc ctcgcagatc aacctcatcc ttctggaacg cctgtggtat
1381 gttatgctgg agcagttcct catgaagtat gtgtggagcg cctcgggcct gctcatggtg
1441 gctgtcccca tcatcactgc cactggctac tcagagtcag atgcagaggc cgtgaagaag
1501 gcagccttgg aaaagaagga ggaggagctg gtgagcgagc gcacagaagc cttcactatt
1561 gcccgcaacc tcctgacagc ggctgcagat gccattgagc ggatcatgtc gtcgtacaag
1621 gaggtgacgg agctggctgg ctacacagcc cgggtgcacg agatgttcca ggtatttgaa
1681 gatgttcagc gctgtcactt caagaggccc agggagctag aggacgctca ggcggggtct
1741 gggaccatag gccggtctgg tgtccgtgtg gagggccccc tgaagatccg aggccaggtg
1801 gtggatgtgg aacagggggat catctgcgag aacatcccca tcgtcacgcc ctcaggagag
1861 gtggtggtgc cagcctcaa catcagggtg gaggaaggca tgcatctgct catcacaggc
1921 cccaatggct gcggcaagag ctccctgttc cggatcctgg gtgggctctg gcccacgtac
1981 ggtggtgtgc tctacaagcc cccacccag cgcatgttct acatcccgca gaggccctac
2041 atgtctgtgg gctccctgcg tgaccaggtg atctacccgg actcagtgga ggacatgcaa
2101 aggaagggct actcggagca ggacctggaa gccatcctgg acgtcgtgca cctgcaccac
2161 atcctgcagc gggagggagg ttgggaggct atgtgtgact ggaaggacgt cctgtcgggt
2221 ggcgagaagc agagaatcgg catggcccgc atgttctacc acaggcccaa gtacgccctc
2281 ctggatgaat gcaccagcgc cgtgagcatc gacgtggaag caagatctt ccaggcggcc
2341 aaggacgcgg gcattgccct gctctccatc acccaccggc cctccctgtg aaataccac
2401 acacacttgc tacagttcga tggggagggc ggctggaagt tcgagaagct ggactcagct
2461 gcccgcctga gctgacgga ggagaagcag cggctggagc agcagctggc gggcattccc
2521 aagatgcagc ggcgcctcca ggagctctgc cagatcctgg gcgaggccgt ggccccagcg
2581 catgtgccgg cacctagccc gcaaggccct ggtggcctcc agggtgcctc cacctgacac
2641 aaccgtcccc ggccctgcc ccgcccccaa gctcggatca catgaaggag acagcagcac
2701 ccacccatgc acgcaccccg cccctgcatg cctggcccct cctcctagaa aacccttccc
2761 gccctcggga aagtagatgt ggagggtggc gccctgcgta accctcgccc tgtccctccc
2821 actccctggg ggcgctgttc cacagtgact gggccctgtc cagggcagtg agtcctctac
2881 tttgctccgt ggaggaagct ggggtacaag gggcccagtg ctggcacac agcagcgcag
2941 ccgagcccca ggagcccgtc aggccacagc ccctggcact gcaggtggcc tccctccaga
3001 gactcgagtc cccatgattc cctcctcgtc agtctctcaa agaccccatg gtccatcccc
3061 tgagggtggt cagccaaggc tcccgttccg tgggatgcca taaaagccgc ccagtgggac
3121 ccacagtcac acagagcgcc tcacctgcat cctctccccc acaagagccc caaagatccc
3181 acgggagagg ggagagggac gcacagcact gcctgccaag cgagaatgca ggccccgccc
3241 cctcggcccc tcaccacctc tttctacagc ctaatttatt ggattcccta ttcgtagcca
3301 tctccgtggc caatgtgact accgtgccag cagcgggggc ggcccagcct ctgagtcccg
3361 tggggccccg gctcccaccg gtgccaaacc cagcccctgc ggccgtcacc ccgccagcct
3421 acactgccag ccgccaccgg ggcacacggg cctctgcttg ccagccagga gtgcggacac
3481 catgttccca gctcagtgcc aaagagggg caccaggggg agctgtctgc ggagccagcg
3541 cctgcccgag agagacccca ccgccaccgt gtgccttcc cgggccctca gccctcgggc
```

-continued
```
3601 cgggcaccac ccccagtccc cccagtaaaa gcctccactg gcaaatgcag tccttcctcc 3661 ctgcaaaaaa aaaaaaaaaa aaaaaaaaaa aaaaaa
```

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

The term "antibody," as used herein, refers to an immunoglobulin molecule which specifically binds with an antigen. The term "antibody fragment" refers to a portion of an intact antibody and refers to the antigenic determining variable regions of an intact antibody.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a protein or nucleic acid that is substantially identical to a reference protein or nucleic acid. In some embodiments the portion retains at least 50%, 75%, or 80%, or more preferably 90%, 95%, or even 99% of the biological activity of the reference protein or nucleic acid described herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein "peroxisomal disease" refers to any of a group of diseases resulting from abnormal metabolism leading to accumulation of a substrate (for example very long chain fatty acids) in the peroxisome. For example, peroxisomal diseases are caused by peroxisomal dysfunction, including as a consequence of deficiency of an enzyme required for the metabolism of lipids or polypeptides for biogenesis.

By "marker" is meant any clinical indicator, protein, metabolite, or polynucleotide having an alteration associated with a disease, disorder, or condition. In various embodiments, a marker of peroxisomal disease is an elevated level of metallothionein polypeptides and/or polynucleotides.

By "metallothionein (MT) polypeptide" is meant a polypeptide or fragment thereof having at least about 85% or greater sequence identity to the amino acid sequence provided at NCBI Accession No. NP_005937 (metallothionein-1A; MT1A), NP_005938 (metallothionein-1B; MT1B), NP_783316 (metallothionein-1E; MT1E), NP_005940 (metallothionein-1F; MT1F), NP_005941 (metallothionein-1G; MT1G), NP_005942 (metallothionein-1H; MT1H), (metallothionein-1I pseudogen; MT1Ip MTE), (metallothionein-1L; MT1L or MT1R), NP_789846 (metallothionem-1M; MT1M or MT1K), NP_005943 (metallothionein-1X; MT1X), NP_005944 (metallothionein-2; MT2 or MT2A), NP_005945 (metallothionein-3; MT3), or NP_116324 (metallothionein-4; MT4), as provided below, and having metal ion binding activity.

NP_005937 (metallothionein-1A; MT1A)
(SEQ ID NO: 3)
```
1   mdpncscatg gsctctgsck ckeckctsck ksccsccpms cakcaqgcic kgasekcscc 61  a
```

NP_005938 (metallothionein-1B; MT1B)
(SEQ ID NO: 4)
```
1   mdpncscttg gscacagsck ckeckctsck kcccsccpvg cakacqgcvc kgssekcrcc 61  a
```

NP_783316 (metallothionein-1E; MT1E)
(SEQ ID NO: 5)
```
1   mdpncscatg gsctcagsck ckeckctsck ksccsccpvg cakcaqgcvc kgasekcscc 61  a
```

NP_005940 (metallothionein-1F; MT1F)
(SEQ ID NO: 6)
```
1   mdpncscaag vsctcagsck ckeckctsck ksccsccpvg cskcaqgcvc kgasekcscc 61  d
```

NP_005941 (metallothionein-1G; MT1G)
(SEQ ID NO: 7)
```
1   mdpncscaag vsctcassck ckeckctsck ksccsccpvg cakcaqgcic kgasekcscc 61  a
```

NP_005942 (metallothionein-1H; MT1H)
(SEQ ID NO: 8)
```
1   mdpncsceag gscacagsck ckkckctsck ksccsccplg cakcaqgcic kgasekcscc 61  a
```

NP_789846 (metallothionein-1M; MT1M)
(SEQ ID NO: 9)
```
1   mdpncscttg vscactgsck ckeckctsck ksccsccpvg cakcahgcvc kgtlencscc 61  a
```

NP_005943 (metallothionein-1X; MT1X)
(SEQ ID NO: 10)
```
1   mdpncscspv gscacagsck ckeckctsck ksccsccpvg cakcaqgcic kgtsdkcscc 61  a
```

NP_005944 (metallothionein-2; MT2)
(SEQ ID NO: 11)
```
1   mdpncscaag dsctcagsck ckeckctsck ksccsccpvg cakcaqgcic kgasdkcscc 61  a
```

NP_005945 (metallothionein-3; MT3)
(SEQ ID NO: 12)
```
1   mdpetcpcps ggsctcadsc kcegckctsc kksccsccpa ecekcakdcv ckggeaaeae 61  aekcsccq
```

NP_116324 (metallothionein-4; MT4)
(SEQ ID NO: 13)
```
1   mdprecvcms ggicmcgdnc kcttcncktc rksccpccpp gcakcargci ckggsdkcsc 61  cp
```

By "metallothionein (MT) polynucleotide" is meant a nucleic acid molecule having at least about 85% or greater sequence identity to the nucleic acid sequence provided at NCBI Accession No. NM_005946 (metallothionein-1A; MT1A), NM_005947 (metallothionein-1B; MT1B), NM_175617 (metallothionein-1E; MT1E), NM_005949 (metallothionein-1F; MT1F), NM_005950 (metallothionein-1G; MT1G), NM_005951 (metallothionein-1H; MT1H), NR_003669 (metallothionein-1I pseudogene; MT1Ip or MTE), NR_001447 (metallothionein-1L; MT1L or MT1R), NM_176870 (metallothionem-1M; MT1M or MT1K), NM_005952 (metallothionein-1X; MT1X), NM_005953 (metallothionein-2; MT2 or MT2A), NM_005954 (metallothionein-3; MT3), or NM_032935 (metallothionein-4; MT4), as provided below, and encoding a metallothionein polypeptide.

NM_005946 (metallothionein-1A; MT1A)
(SEQ ID NO: 14)
```
  1  accaagcctt ccacgtgcgc cttatagcct ctcaacttct tgcttgggat ctccaacctc
 61  accgcggctc gaaatggacc ccaactgctc ctgcgccact ggtggctcct gcacctgcac
121  tggctcctgc aaatgcaaag agtgcaaatg cacctcctgc aagaagagct gctgctcctg
181  ctgccccatg agctgtgcca agtgtgccca gggctgcatc tgcaaggggg catcagagaa
241  gtgcagctgc tgtgcctgat gtccggacag ccctgctcga agatatagaa agagtgacct
301  gcacaaactt ggaatttttt ttccatacaa ccctgaccca tttactgtat ttttttttaat
361  gaaatatgtg aatgataata aaagttgctg acttaaaaaa aaaaaaaaaa aaaaaaaaaa
421  aaaaaaaaaa aaaaaaaaaa aaaaaaaaaa aaaaaaaaaa aaaaaaa
```

NM_005947 (metallothionein-1B; MT1B)
(SEQ ID NO: 14)
```
  1  accaagcctt ccacgtgcgc cttatagcct ctcaacttct tgcttgggat ctccaacctc
 61  accgcggctc gaaatggacc ccaactgctc ctgcgccact ggtggctcct gcacctgcac
121  tggctcctgc aaatgcaaag agtgcaaatg cacctcctgc aagaagagct gctgctcctg
181  ctgccccatg agctgtgcca agtgtgccca gggctgcatc tgcaaggggg catcagagaa
241  gtgcagctgc tgtgcctgat gtccggacag ccctgctcga agatatagaa agagtgacct
301  gcacaaactt ggaatttttt ttccatacaa ccctgaccca tttactgtat ttttttttaat
361  gaaatatgtg aatgataata aaagttgctg acttaaaaaa aaaaaaaaaa aaaaaaaaaa
421  aaaaaaaaaa aaaaaaaaaa aaaaaaaaaa aaaaaaaaaa aaaaaaa
```

NM_175617 (metallothionein-1E; MT1E)
(SEQ ID NO: 15)
```
  1  aggaacgcgg gcggtgcgga ctcagcgggc cgggtgcagg cgcggagctg ggcctctgcg
 61  cccggcccga cctccgtcta taaatagagc agccagttgc agggctccat tctgctttcc
121  aactgcctga ctgcttgttc gtctcactgg tgtgagctcc agcatcccct ttgctcgaaa
181  tggacccccaa ctgctcttgc gccactggtg gctcctgcac gtgcgccggc tcctgcaagt
241  gcaaagagtg caaatgcacc tcctgcaaga agagctgctg ttcctgctgc cccgtgggct
301  gtgccaagtg tgcccagggc tgcgtctgca aggggcatc ggagaagtgc agctgctgtg
361  cctgatgtgg gaacagctct tctcccagat gtaaatagaa caacctgcac aacctggatt
421  tttttaaaaa tacaacactg agccatttgc tgcatttctt tttatactaa atatgtgact
481  gacaataaaa acaattttga ctttaaaaaa aaaaaaaaa
```

NM_005949 (metallothionein-1F; MT1F)
(SEQ ID NO: 16)
```
  1  gcccccctccc ctgactatca aagcagcggc cggctgttgg ggtccaccac gccttccacc
 61  tgccccactg cttcttcgct ctctctcttgg aaagtccagt ctctcctcgg cttgcaatgg
121  accccaactg ctcctgcgcc gctggtgtct cctgcacctg cgctggttcc tgcaagtgca
181  aagagtgcaa atgcacctcc tgcaagaaga gctgctgctc ctgctgcccc gtgggctgta
241  gcaagtgtgc ccagggctgt gtttgcaaag gggcgtcaga gaagtgcagc tgctgcgact
301  gatgccagga caacctttct cccagatgta aacagagaga catgtacaaa cctggatttt
361  ttttttatac caccttgacc catttgctac attccttttc ctgtgaaata tgtgagtgat
421  aattaaacac tttagacctg aaaaaaaaaa aaaaaa
```

NM_005950 (metallothionein-1G; MT1G)
(SEQ ID NO: 17)
```
  1  actccgcctt ccacgtgcac ccactgcctc ttcccttctc gcttgggaac tctagtctcg
 61  cctcggggttg caatggaccc caactgctcc tgtgccgctg tgtctcctg cacctgcgcc
121  agctcctgca agtgcaaaga gtgcaaatgc acctcctgca agaagagctg ctgctcctgc
```

-continued

```
    181 tgccctgtgg gctgtgccaa gtgtgcccag gctgcatct gcaaggggc atcggagaag 241 tgcagctgct gcgcctgatg tcgggacagc cctgctccca agtacaaata gagtgacccg 301 taaaatccag gattttttgt tttttgctac aatcttgacc cctttgctac attccttttt 361 ttctgtgaaa tatgtgaata ataattaaac acttagactt gaaaaaaaaa aaaaaaaaa
```

NM_005951 (metallothionein-1H; MT1H)

(SEQ ID NO: 18)

```
      1 accacgccct ccacgtgttc cactgcctct tctcttctcg cttgggaact ccagtctcac 61 ctcggcttgc aatggacccc aactgctcct gcgaggctgg tggctcctgc gcctgcgccg 121 gctcctgcaa gtgcaaaaag tgcaaatgca cctcctgcaa gaagagctgc tgctcctgtt 181 gcccctggg ctgtgccaag tgtgcccagg ctgcatctg caaggggcg tcagagaagt 241 gcagctgctg tgcctgatgt cgggacagcc ctgctgtcag atgaaaacag aatgacacgt 301 aaaatccagg atttttttt tctacaactc cgactcattt gctacattcc tttttttctg 361 tgaaatatgt gaataataat taaacactta gacttga
```

NR_003669 (metallothionein-H pseudogene; MT1Ip or MTE)

(SEQ ID NO: 19)

```
      1 tccaccacgc ctcccacctg ccccactgct tcttctcctc tcccttagga actctagctt 61 cacctcgctt cgtaatggac cccaattgct cctgctccac tactcctgca aatgcagaga 121 gtgcaaatgc acctcctgca agacgagctg ctgctcctgc tgccccgtgg gctgtgccaa 181 gtgtgcccag ggatgtgttt gcaaagggac actgacaagt gcagctgctg ctcctgatgt 241 agggaaagct gtgttcccag aagtagaaag tgtacaaacc tggaattgtt ttccatacaa 301 ccctgaccca ttagtacatt tgggtttcta aaaataaaat atgttaatga taataaaagt 361 tgactttatt ct
```

NR_001447 (metallothionein-1L; MT1L or MT1R)

(SEQ ID NO: 20)

```
      1 gtcccatctc cgcctgcaaa aggagcagct ggctccaggc tccaacgtgc cttccagctg 61 cctgactgcc tcttcgcctc tcccgtcatt tcttggctcg aaatggaccc caactgctcc 121 tgcgccactg ggggctcctg ctcctgtgcc agctcctgca agtgcaaaga gtgcaaatga 181 acctcctgca agaagagctg ctgctcctgc tgccccatgg gctgtgccaa gtgtgcccag 241 ggctgcgtct gcaaggggc gtcggagaag tgcagctgct gtgcctgatg tggggacagc 301 cctgctccca gatgtaaaca gagcaacctg cacaaacctg gattttttt tcatacaacc 361 ctgagcattt gctacattcc tttttctatt aaatatgtaa acgacaataa aacagttttg 421 acttgaaaaa aaaaaaaaa aaa
```

NM_176870 (metallothionein-1M; MT1M)

(SEQ ID NO: 21)

```
      1 ccctgagtag aaaagcagcc gcaggctgtg gcgctccacc acgccgtccg ggtgggccta 61 gcagtcgctc catttatcgc ttgagatctc cagccttacc gcggctcgaa atggacccca 121 actgctcctg caccactggt gtctcctgcg cctgcaccgg ctcctgcaag tgcaaagagt 181 gcaaatgcac ctcctgcaag aagagctgct gctcctgctg cccgtgggc tgtgccaagt 241 gtgcccacgc tgtgtctgc aaagggacgt tggagaactg cagctgctgt gcctgatgtg 301 ggaacagctc ttctcccaga tgttaataga acaagctgca caacctggat tttttttcaa
```

-continued

```
361  tacgatactg agccatttgc tgcatttctt tttatattaa atatgtgagt gacaataaaa 421  caattttgac ttgaatctta aaaaaaaaaa aaaaaaaaa aaaa
```

NM_005952 (metallothionein-1X; MT1X)
(SEQ ID NO: 22)
```
  1  accacgcttt tcatctgtcc cgctgcgtgt tttcctcttg atcgggaact cctgcttctc 61  cttgcctcga aatggacccc aactgctcct gctcgcctgt tggctcctgt gcctgtgccg 121  gctcctgcaa atgcaaagag tgcaaatgca cctcctgcaa gaagagctgc tgctcctgct 181  gccctgtggg ctgtgccaag tgtgcccagg gctgcatctg caagggacg tcagacaagt 241  gcagctgctg tgcctgatgc caggacagct gtgctctcag atgtaaatag agcaacctat 301  ataaacctgg atttttttt tttttttttt tgtacaaccc tgacccgttt gctacatctt 361  tttttctatg aaatatgtga atggcaataa attcatctag actaaaaaaa aaaaaaaaa 421  aaaaaaaaaa aaaaaaaaaa aaaaaaaaaa aaaaaaaaaa aaaaaaa
```

NM_005953 (metallothionein-2; MT2)
(SEQ ID NO: 23)
```
  1  cttgccgcgc tgcactccac cacgcctcct ccaagtccca gcgaacccgc gtgcaacctg 61  tcccgactct agccgcctct tcagctcgcc atggatccca actgctcctg cgccgccggt 121  gactcctgca cctgcgccgg ctcctgcaaa tgcaaagagt gcaaatgcac ctcctgcaag 181  aaaagctgct gctcctgctg ccctgtgggc tgtgccaagt gtgcccaggg ctgcatctgc 241  aaagggcgt cggacaagtg cagctgctgc gcctgatgct gggacagccc cgctcccaga 301  tgtaaagaac gcgacttcca caaacctgga tttttatgt acaaccctga ccgtgaccgt 361  ttgctatatt ccttttcta tgaaataatg tgaatgataa taaaacagct ttgacttgaa 421  aaaaaaaaaa aaaaaaaaaa aaaaaaaaaa aaaaaaaaaa aaaaaa
```

NM_005954 (metallothionein-3; MT3)
(SEQ ID NO: 24)
```
  1  cccggcagtg cacacacacg gcaggggcgg gcgacagatg cagtgcgtgc gccggagccc 61  aagcgcacaa acgaaagag cgggcgcggt gcgcagggc gggcgcccag cgggcttggc 121  atgcgcgccc ccgcccgagg ctataaaagc atcgccacct gctgccacta gccaagccgc 181  gcgtccagtt gcttggagaa gcccgttcac cgcctccagc tgctgctctc ctcgacatgg 241  accctgagac ctgcccctgc ccttctggtg gctcctgcac ctgcgcggac tcctgcaagt 301  gcgagggat caaatgcacc tcctgcaaga agagctgctg ctcctgctgc cctgcggagt 361  gtgagaagtg tgccaaggac tgtgtgtgca aaggcggaga ggcagctgag gcagaagcag 421  agaagtgcag ctgctgccag tgagaaggca cccctccgtg tggagcacgt ggagatagtg 481  ccaggtggct cagtgccacc tatgcctgtg gtgaagtgtg gctggtgtcc ccttcccctg 541  ctgaccttgg aggaatgaca ataaatccca tgaacagcat gaaaaaaaaa aaaaaaaa
```

NM_032935 (metallothionein-4; MT4)
(SEQ ID NO: 25)
```
  1  atggggagcc tctggctgct gctcactcag cctcccttcc ccagccgtga cagcactgga 61  gcctttcgga cacctggacc atggacccca gggaatgtgt ctgcatgtct ggaggaatct 121  gcatgtgtgg agacaactgc aaatgcacaa cctgcaactg taaacatgt cggaagagct 181  gctgtccctg ctgcccccg ggctgtgcca aatgtgcccg gggctgcatc tgcaaaggag 241  gctcagacaa gtgcagctgc tgcccatgaa agccatccat cgtgcccacc cctt
```

As used herein "neurodegenerative disease" refers to a disease characterized by the progressive loss of structure and/or function of neurons, including death of neurons.

By "peroxisomal disease" is meant a disease characterized by disruption of peroxisomal function or peroxisomal biogenesis resulting in the accumulation of incompletely degraded substrates (e.g., very long chain fatty acid) in the peroxisome. Exemplary peroxisomal diseases include without limitation adrenoleukodystrophy, adrenomyeloneuropathy, and Zellweger syndrome.

By "increasing proliferation" is meant increasing cell division of a cell in vivo or in vitro.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

By "reduces" is meant a negative alteration of at least 10%, 25%, 50%, 75%, or 100%.

By "reference" is meant a standard of comparison or control condition.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.10% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "specifically binds" is meant a compound (e.g., peptide) that recognizes and binds a molecule (e.g., polypeptide), but which does not substantially recognize and bind other molecules in a sample, for example, a biological sample.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

FIG. 1C depicts an example of western blot analysis on cALD grey and white matter samples, compared to a HD sample. FIG. 1D is a graph showing total mRNA abundance of MT transcripts in white matter (WM) and grey matter (GM) of the frontal cortex of 4 cALD, 4 AMN patients and 4 controls. (*** p value 0.001 analyzed with one-way Anova Bonferroni correction) FIG. TE is a graph showing relative mRNA abundance of the indicated 4 different MT isoforms (MT1A, MT1E, MT2A and MT1G) in WM and GM of the frontal cortex of 4 cALD, 4 AMN patients and 4 controls. Data are also shown as total of all patients' categories averaged together in the column ABCD+/−(mean±SEM; * pvalue 0.05 analysed with one-way Anova Bonferroni correction).

FIG. 2A is a graph showing total mRNA abundance of MT transcripts analyzed by quantitative polymerase chain reaction on PAX-gene blood samples from the following patients cohorts: asymptomatic female carriers of ABCD gene mutations (n=12); AMN male symptomatic patients (n=6); cALD pre/early symptomatic patients (n=10); cALD patients post hematopoietic stem cell transplant (n=3). Data are also shown as total of all patients' categories averaged together in the column ABCD+/− in order to show a general trend of over-expression (mean±SEM; * p value 0.01 and 0.001 analyzed with one-way Anova Bonferroni correction). FIG. 2B is a graph showing total mRNA abundance of MT transcripts analyzed by quantitative polymerase chain reaction on T lymphoctyes obtained in culture with stimulation with PHA coming from the same patients' already described. Data are also shown as total of all patients' categories averaged together in the column ABCD+/− in order to show a general trend of over-expression (mean±SEM; one-way Anova, ns). FIG. 2C is a graph showing relative mRNA abundance of 4 different MT isoforms (MT1A, MT1E, MT2A and MT1G) on PAXgene blood samples from the same patients described in FIG. 2A. FIG. 2D is a graph showing relative mRNA abundance of 4 different MT isoforms (MT1A, MT1E, MT2A and MT1G) on PHA stimulated T cells from the same patients described in FIGS. 2A and 2C.

DETAILED DESCRIPTION OF THE INVENTION

Figure 1A:
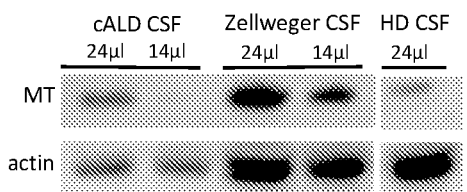
FIGS. 1A-1E show that metallothioneins (MTs) are markers of nervous tissue damage in ALD. FIG. A depicts Western blot immunoreactivity for MT proteins on samples from 4 cerebrospinal fluid samples from 2 ALD patients (UMB_5591 and UMB_1195), one affected by Zellweger Syndrome (neonatal ALD, UMB 4658) and one healthy donor (HD) control sample at two different loading volumes (24 and 14 µl). α-actin immunoreactivity for MT proteins was assessed as control for protein loading. FIG. TB is a graph depicting quantification data noirmalized to α-actin for 2 independent experiments (considering only the loading volume of 24 µl). Total samples analyzed n=2.
Figure 1B:
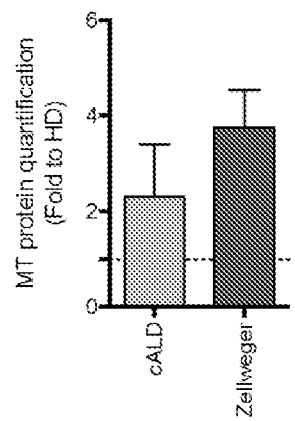

The invention features compositions and methods for the treatment and prevention of peroxisomal diseases (e.g., neonatal adrenoleukodystrophy and Zellweger syndrome), including in a subject selected as having a risk of developing severe CNS damage by measurement of increased levels of metallothionein polypeptides. In some embodiments, the methods involve HSC transplantation, including ablating and/or reconstituting microglia. In some embodiments, allogeneic hematopoietic stem cell transplant (HCT) is used to supply cells that produce functional ALDP. The invention also features compositions and methods for the diagnosis of a subject having a peroxisomal disease with severe and rapidly progressive brain damage involving detecting increased levels of metallothionein polypeptides or polynucleotides.

The present invention is based at least in part on the discoveries described herein, including the observation that subjects having peroxisomal disease have increased levels of metallothionein polypeptides. Current methods for treating peroxisomal diseases using HSC transplantation are not effective on CNS disease manifestations when applied to symptomatic patients with rapidly progressive disease because of the slow replacement of resident microglia by the progeny of the transplanted cells. Even patients transplanted in early disease stages develop long-term disease manifestations mostly related to neurodegeneration. Importantly, disease causing mutations in the ABCD1 protein gene do not per se allow prediction of the occurrence of cerebral ALD versus adrenomyeloneuropathy, or the occurrence of cerebral disease early in childhood or later in adult age. In the presence of newborn screening programs being activated for ALD, the availability of a marker or occurrence of brain disease in positive patients would be of great value for identifying those who may benefit from HSC-based transplant approaches (either allogeneic stem cell transplant or HSC gene therapy). Indeed, these therapeutic modalities are associated with risks, morbidity and some mortality and are only indicated for patients with cerebral disease at present. Importantly, HSC-based approaches could be complemented by neuroprotective and immunomodulating interventions to guarantee a better long term prognosis for the treated patients. Finally, patients with cerebral disease who are not eligible to HSC transplantation or gene therapy may benefit from therapeutic interventions aimed at relenting their disease progression.

Therefore, the present invention has the potential to provide i) means of early diagnosis of cerebral involvement in molecularly identified ALD subjects having high MT levels in samples and ii) opportunity for therapy (e.g., HSC transplantation) in order to mitigate neurodegeneration and neuroinflammation/oxidative stress associated with the disease.

Metallothioneins (MTs)

In one aspect, the invention is directed to a method of diagnosing active cerebral involvement in a subject affected with a peroxisomal disease by measuring increased levels of metallothionein polypeptides in a biological sample from the subject. Metallothioneins (MTs) are a family of small (~6-7 kDa), heat-resistant proteins containing 25-30% cysteine residues that are evolutionarily highly conserved in a broad range of species from yeast to mammals. MTs are up-regulated by glucocorticoids, oxidative stress and a variety of heavy metals, such as copper, cadmium, mercury and zinc (Andrews (2000) Biochem. Pharmacol. 59, 95-104). Isoforms range from MT-1 to MT-4 and have slightly different amino acid composition. MTs bind metals and protect against their toxicity, as was first demonstrated in aquatic species, such as fish, arthropods and molluscs from contaminated waters. Apart from binding heavy metals, MTs are considered to act as antioxidants, although by undetermined mechanisms. Thus MTs have been found to protect against apoptosis/necrosis induced by oxidative stress, etoposide, cisplatin, doxorubicin and X-irradiation (Cai et al. (2004) Toxicol. Lett. 146, 217-226; Chimienti et al. (2001) Free Radicals Biol. Med. 31, 1179-1 190; Wang et al. (2001) J. Pharmacol. Exp. Ther. 298, 461-468).

The MT transcript and protein described herein may be selected from, for example, metallothionein-1A (MT1A), metallothionein-1B (MT1B), metallothionein-1E (MT1E), metallothionein-1F (MT1F), metallothionein-1G (MT1G), metallothionein-1H (MT1H), metallothionein-1I pseudogene (MT1Ip or MTE), metallothionein-1L (LT1L or MT1R), metallothionem-1M (MT1M or MT1K), metallothionein-1X (MT1X), metallothionein-2 (MT2), metallothionein-2A (MT2A), metallothionein-3 (MT3) or metallothionein-4 (MT4).

The NCBI protein accession numbers of the main members of the family are: NP_005937 (MT1A); NP_005938 (MT1B); NP_783316 (MT1E); NP_005940 (MT1F); NP_005941 (MT1G); NP_005942 (MT1H); NP_789846 (MT1M); NP_005943 (MT1X); NP_005944 (MT2); NP_005945 (MT3); and NP_116324 (MT4). Further NCBI accession numbers for MT1A, MT1E, MT2A and MTE-MT1IP include: NM 005946, NM_075617, NM_005953 and NR 003669, respectively.

Peroxisomal Diseases

Peroxisomal diseases comprise a class of inherited diseases characterized by disruption of normal peroxisomal function or biogenesis resulting in the accumulation of incompletely degraded substrates (e.g., very long chain fatty acid) that have been targeted for degradation after endocytosis or autophagy. The ensuing accumulation of the substrate itself or of the product(s) of an alternative metabolic route affects the architecture and function of the cells, leading to cell dysfunction or death. Further, the primary defect is frequently exacerbated by secondary responses. This is of particular relevance in the Central Nervous System (CNS) where neuroinflammation occurs representing a primary reaction to substrate accumulation within microglia and astrocytes and/or an inflammatory response to primary neuronal or oligodendroglial damage. Examples of peroxisomal diseases include adrenoleukodystrophy and Zellweger syndrome.

X-Linked Adrenoleukodystrophy (X-ALD)

X-linked adrenoleukodystrophy (X-ALD) is a metabolic genetic disease with a frequency of 1:12.000 males. It mainly affects the nervous system and the adrenal glands. In this disorder, myelin is prone to deterioration (demyelination). In addition, damage to the outer layer of the adrenal glands (adrenal cortex) causes adrenocortical insufficiency. There are three distinct types of X-linked adrenoleukodystrophy: a childhood cerebral form, an adrenomyeloneuropathy type, and a form called Addison disease only.

The disease in all the variants is due to mutations in the ABCD1 gene that is located in the chromosome Xq28; mutations determine the loss of function of the related ALD protein which in turns results in the accumulation of unbranched saturated very long chain fatty acids (VLCFAs) within phospholipid fractions such as lysophatidylcholine (LPC), particularly in brain and adrenal cortex. There is not a reliable genotype-phenotype correlation that could allow predicting the clinical variants of molecularly diagnosed patients.

Phenotypic variability in X-ALD appears to be linked to brain inflammation that causes progressive neurological decline mostly in children but also in adults with X-ALD. Without being bound by theory, the initiation of cerebral demyelination could be linked to the amount of VLCFA in complex lipids and to their inefficient degradation by microglia cells. Thus, despite perivascular macrophages were shown to closely follow the leading edge of the demyelinating lesion and to play a crucial role in the removal of myelin debris, microglia cells behaved differently, being few in the same area and apoptotic in the surrounded ones[13]. Eichler et al speculated that microglia in this region are unable to degrade VLCFA that in turns may cause microglial activation and apoptosis. The loss of microglia and/or microglia dysfunction may play an important role in the early phases of demyelination mainly due to the production of pro-inflammatory cytochines (CCL2, CCL4, IL-1a, CXCL8) and to the altered ability to provide neuroprotective factors to deficient oligodendrocytes. In this scenario microglia cells may be an appropriate target for intervention in X-ALD patients with evidence of cerebral demyelination.

Childhood Cerebral Adrenoleukodystrophy (CCALD)

The incidence of x-linked adrenoleukodystrophy (ALD) in the United States is about 1:21,000 male births with about 35% developing CCALD; about 35 to 40 boys are diagnosed with CCALD each year. Childhood cerebral adrenoleukodystrophy (CCALD) has a median age of onset age 7; range 3-15 years; when left untreated, leads to a vegetative state, and ultimately death, within a median of 5 years after diagnosis. CCALD often initially presents as Addison's disease, but the diagnosis is usually made based on "sudden" decreases in attention, thinking, concentration, and other cerebral functions with confirmatory findings of cerebral demyelination on magnetic resonance imaging (MRI). Prior to demyelination, the MRI of the patient's brain is normal, and there are no neurodevelopmental abnormalities. The clinical course may be "slow" at first, but can become rapidly progressive and irreversible with the widespread loss of myelin in the brain. The terms "slow" and "sudden" are relative in that the duration of demyelination is not truly known, but the rapid decrease in cognitive and motor function can happen at any time and for unknown reasons. Indeed, the MRI changes precede symptoms, and can be floridly abnormal with widespread demyelination at a time when there are very few clinical manifestations of the disease.

The only available treatment for CCALD is allogeneic hematopoietic stem cell transplant (HCT) to supply cells that produce functional ALDP. Since the brain microglia are derived from the bone marrow, fully matched related donor human stem cell transplantation using cells producing functional ALDP can potentially ameliorate or stop the progression of demyelination. However, because it takes 12 to 18 months for allogeneic HCT to stabilize the disease, and because of the progressive nature of the disease, transplantation should be done as soon as possible upon diagnosis. This is sometimes problematic because of the lead times needed to find related or unrelated matched bone marrow stem cell donors. The use of allogeneic stem cells also presents a risk of graft failure and the development of acute and chronic graft versus host disease (GvHD). These complications can lead to death and are increased in incidence when unrelated donors are utilized as a source for allogeneic hematopoietic stem cells.

Another source of ALDP replacement is the use of matched are, more typically, partially matched cord blood cell transplants. The use of cord blood stem cells (CBSCs) is problematic, with a risk of graft failure and prolonged time to engraftment requiring extended transfusion support. Indeed, all forms of allogeneic HCT involve a 10-15% risk of transplant related mortality, and up to a 30% risk of chronic graft versus host disease. More recently, HSC gene therapy[1] has also been explored as treatment options for X-ALD.

Adrenomyeloneuropathy

Adrenomyeloneuropathy (AMN) is a form of X-ALD. AMN patients generally have spinal cord dysfunction, which leads to the initial symptoms that include difficulties in walking or a change in the walking pattern. The average age at which symptoms first appear is 28, but onset can occur anywhere from the second to the fifth decades of life.

AMN can be broken down into two general clinical forms: AMN with cerebral involvement (the spinal cord and brain are both affected), and AMN without cerebral involvement (only the spinal cord is affected). Of patients with AMN, approximately 54% have normal brain function, while 46% have brain involvement of varying degrees.

AMN without Cerebral Involvement

These patients have a significantly better prognosis than those with cerebral involvement. In general, neuropsychological function is normal except for mild deficits in motor speed and visual memory. Physical therapy, management of the problems with urinary control, and counseling are recommended for men with AMN. If there is no cerebral involvement, it is possible for men with AMN to maintain successful personal and professional lives.

AMN with Cerebral Involvement

Those AMN patients with cerebral involvement have a poorer prognosis than those without cerebral involvement. In approximately 20% of patients with AMN, brain involvement is severely progressive and leads to serious cognitive and behavioral disturbances that eventually may progress to total disability and death.

Adult Cerebral ALD

Adult cerebral ALD is relatively rare, only representing approximately 3% of all ALD cases. Age of onset varies from the twenties to the fifties. The symptoms are similar to those of schizophrenia with dementia, and the progression of the disorder is rapid. The average time from the initial symptoms to vegetative state or death is approximately 3-4 years.

Neurodegenerative Manifestations in Peroxisome Diseases

Neurodegenerative diseases are characterized by the progressive loss of the structure and/or function of neurons and/or neuronal cell death. Inflammation has been implicated for a role in several neurodegenerative diseases. Progressive loss of motor and sensory neurons and the ability of the mind to refer sensory information to an external object is affected in different kinds of neurodegenerative diseases.

A health care professional may diagnose a subject as having a neurodegenerative disease by the assessment of one or more symptoms of a neurodegenerative disease in the subject. Non-limiting symptoms of a neurodegenerative disease in a subject include difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; and changes in appetite. A health care professional may also base a diagnosis, in part, on the subject's family history of a neurodegenerative disease. A health care professional may diagnose a subject as having a neurodegenerative disease upon presentation of a subject to a health care facility (e.g., a clinic or a hospital). In some instances, a health care professional may diagnose a subject as having a neurodegenerative disease while the subject is admitted in an assisted care facility. Typically, a physician diagnoses a neurodegenerative disease in a subject after the presentation of one or more symptoms.

Methods of Treatment

The present invention provides methods of identifying patients candidate to CNS-targeted treatments because showing or likely to develop brain damage and of treating disease and/or disorders or symptoms in these subjects thereof which comprise administering a therapeutically effective amount of a pharmaceutical composition comprising a therapeutic agent. Thus, one embodiment is a method of identification of patients bearing ABCD1 gene mutations at risk of developing or already having cerebral manifestations of adrenoleukodystrophy. The method includes the step of measuring MT levels (as mRNA or protein) in samples collected from patients bearing ABCD1 mutations in order to determine brain involvement by the disease and potentially its severity. This determination could lead to clinical decision regarding the possibility of activating therapeutic interventions in patients showing high MT levels and cerebral involvement.

The methods also include the possibility of measuring MT levels in patients treated by available theraphies in order to monitor efficacy on the brain that would reslt in reduction of MT expression levels.

Another embodiment is a method for treating a subject suffering from or susceptible to a cerebral disease or disorder or symptom thereof. The method includes the step of administering to the mammal a therapeutic amount of a cell herein sufficient to attenuate the disease or disorder or symptom thereof, under conditions such that the disease or disorder is treated.

The methods herein include administering to the subject (including a subject identified as in need of such treatment) an effective amount of a cell described herein, or a composition described herein to produce such effect. Identifying a subject in need of such treatment can be in the judgment of a subject or a health care professional and can be subjective (e.g. opinion) or objective (e.g. measurable by a test or diagnostic method). Administration could be performed using autologous HSCs, e.g. in the context of HSC gene therapy approaches aimed at restoring ABCD1 function, as in the case of the on going HSC gene therapy trial, or by using viral vectors, e.g. Adenoassociated vectors, delivered either intra-techally or intra-venously.

Identifying a subject in need of such treatment can be in the judgment of a subject or a health care professional and can be subjective (e.g. opinion) or objective (e.g. measurable by a test or diagnostic method). Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

Detection of Biomarkers

The biomarkers of this invention (e.g., metallothionein polypeptides and/or polynucleotides) can be detected by any suitable method. The methods described herein can be used individually or in combination for a more accurate detection of the biomarkers (e.g., biochip in combination with mass spectrometry, immunoassay in combination with mass spectrometry, and the like).

Detection paradigms that can be employed in the invention include, but are not limited to, optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

These and additional methods are described infra.

Detection by Immunoassay

In particular embodiments, the biomarkers of the invention are measured by immunoassay. Immunoassay typically utilizes an antibody (or other agent that specifically binds the marker) to detect the presence or level of a biomarker in a sample. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, Western blot, sandwich immunoassays including ELISA and other enzyme immunoassays, fluorescence-based immunoassays, and chemiluminescence. Nephelometry is an assay done in liquid phase, in which antibodies are in solution. Binding of the antigen to the antibody results in changes in absorbance, which is measured. Other forms of immunoassay include magnetic immunoassay, radioimmunoassay, and real-time immunoquantitative PCR (iqPCR).

Immunoassays can be carried out on solid substrates (e.g., chips, beads, microfluidic platforms, membranes) or on any other forms that supports binding of the antibody to the marker and subsequent detection. A single marker may be detected at a time or a multiplex format may be used. Multiplex immunoanalysis may involve planar microarrays (protein chips) and bead-based microarrays (suspension arrays).

In a SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

Detection by Biochip

In aspects of the invention, a sample is analyzed by means of a biochip (also known as a microarray). The polypeptides and nucleic acid molecules of the invention are useful as hybridizable array elements in a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, hereby incorporated by reference.

Detection by Protein Biochip

In aspects of the invention, a sample is analyzed by means of a protein biochip (also known as a protein microarray). Such biochips are useful in high-throughput low-cost screens to identify alterations in the expression or post-translation modification of a polypeptide of the invention, or a fragment thereof. In embodiments, a protein biochip of the invention binds a biomarker present in a subject sample and detects an alteration in the level of the biomarker. Typically, a protein biochip features a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins (e.g., antibodies that bind a marker of the invention) are spotted on a substrate using any convenient method known to the skilled artisan (e.g., by hand or by inkjet printer).

In embodiments, the protein biochip is hybridized with a detectable probe. Such probes can be polypeptide, nucleic acid molecules, antibodies, or small molecules. For some applications, polypeptide and nucleic acid molecule probes are derived from a biological sample taken from a patient, such as a bodily fluid (such as blood, blood serum, plasma, saliva, urine, ascites, cyst fluid, and the like); a homogenized tissue sample (e.g., a tissue sample obtained by biopsy); or a cell isolated from a patient sample. Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Many protein biochips are described in the art. These include, for example, protein biochips produced by Ciphergen Biosystems, Inc. (Fremont, CA), Zyomyx (Hayward, CA), Packard BioScience Company (Meriden, CT), Phylos (Lexington, MA), Invitrogen (Carlsbad, CA), Biacore (Uppsala, Sweden) and Procognia (Berkshire, UK). Examples of such protein biochips are described in the following patents or published patent applications: U.S. Pat. Nos. 6,225,047; 6,537,749; 6,329,209; and 5,242,828; PCT International Publication Nos. WO 00/56934; WO 03/048768; and WO 99/51773.

Detection by Nucleic Acid Biochip

In aspects of the invention, a sample is analyzed by means of a nucleic acid biochip (also known as a nucleic acid microarray). To produce a nucleic acid biochip, oligonucleotides may be synthesized or bound to the surface of a substrate using a chemical coupling procedure and an ink jet application apparatus, as described in PCT application WO95/251116 (Baldeschweiler et al.). Alternatively, a gridded array may be used to arrange and link cDNA fragments or oligonucleotides to the surface of a substrate using a vacuum system, thermal, UV, mechanical or chemical bonding procedure.

A nucleic acid molecule (e.g. RNA or DNA) derived from a biological sample may be used to produce a hybridization probe as described herein. The biological samples are generally derived from a patient, e.g., as a bodily fluid (such as blood, blood serum, plasma, saliva, urine, ascites, cyst fluid, and the like); a homogenized tissue sample (e.g., a tissue sample obtained by biopsy); or a cell isolated from a patient sample. For some applications, cultured cells or other tissue preparations may be used. The mRNA is isolated according to standard methods, and cDNA is produced and used as a template to make complementary RNA suitable for hybridization. Such methods are well known in the art. The RNA is amplified in the presence of fluorescent nucleotides, and the labeled probes are then incubated with the microarray to allow the probe sequence to hybridize to complementary oligonucleotides bound to the biochip.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., of at least about 37° C., or of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In embodiments, hybridization will occur at 37° C. in 500 mM NaCl, 50 mM trisodium citrate, 1% SDS, 35% formamide, and 100 µg/ml denatured salmon sperm DNA (ssDNA). In other embodiments, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., of at least about 42° C., or of at least about 68° C. In embodiments, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In other embodiments, wash steps will occur at 68 C in 15 mM NaCl, 1.5 mM trisodium citrate, and 0.1% SDS. Additional variations on these conditions will be readily apparent to those skilled in the art.

Detection system for measuring the absence, presence, and amount of hybridization for all of the distinct nucleic acid sequences are well known in the art. For example, simultaneous detection is described in Heller et al., Proc. Natl. Acad. Sci. 94:2150-2155, 1997. In embodiments, a scanner is used to determine the levels and patterns of fluorescence.

Detection by Mass Spectrometry

In aspects of the invention, the biomarkers of this invention are detected by mass spectrometry (MS). Mass spectrometry is a well known tool for analyzing chemical compounds that employs a mass spectrometer to detect gas phase ions. Mass spectrometers are well known in the art and include, but are not limited to, time-of-flight, magnetic sector, quadrupole filter, ion trap, ion cyclotron resonance, electrostatic sector analyzer and hybrids of these. The method may be performed in an automated (Villanueva, et al., *Nature Protocols* (2006) 1(2):880-891) or semi-automated format. This can be accomplished, for example with the mass spectrometer operably linked to a liquid chromatography device (LC-MS/MS or LC-MS) or gas chromatography device (GC-MS or GC-MS/MS). Methods for performing mass spectrometry are well known and have been disclosed, for example, in US Patent Application Publication Nos: 20050023454; 20050035286; U.S. Pat. No. 5,800,979 and the references disclosed therein.

Laser Desorption/Ionization

In embodiments, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of proteins by LDI can take the form of MALDI or of SELDI. The analysis of proteins by LDI can take the form of MALDI or of SELDI.

Laser desorption/ionization in a single time of flight instrument typically is performed in linear extraction mode. Tandem mass spectrometers can employ orthogonal extraction modes.

Matrix-Assisted Laser Desorption/Ionization (MALDI) and Electrospray Ionization (ESI)

In embodiments, the mass spectrometric technique for use in the invention is matrix-assisted laser desorption/ionization (MALDI) or electrospray ionization (ESI). In related embodiments, the procedure is MALDI with time of flight (TOF) analysis, known as MALDI-TOF MS. This involves forming a matrix on a membrane with an agent that absorbs the incident light strongly at the particular wavelength employed. The sample is excited by UV or IR laser light into the vapor phase in the MALDI mass spectrometer. Ions are generated by the vaporization and form an ion plume. The ions are accelerated in an electric field and separated according to their time of travel along a given distance, giving a mass/charge (m/z) reading which is very accurate and sensitive. MALDI spectrometers are well known in the art and are commercially available from, for example, PerSeptive Biosystems, Inc. (Framingham, Mass., USA).

Magnetic-based serum processing can be combined with traditional MALDI-TOF. Through this approach, improved peptide capture is achieved prior to matrix mixture and deposition of the sample on MALDI target plates. Accordingly, in embodiments, methods of peptide capture are enhanced through the use of derivatized magnetic bead based sample processing.

MALDI-TOF MS allows scanning of the fragments of many proteins at once. Thus, many proteins can be run simultaneously on a polyacrylamide gel, subjected to a method of the invention to produce an array of spots on a collecting membrane, and the array may be analyzed. Subsequently, automated output of the results is provided by using an server (e.g., ExPASy) to generate the data in a form suitable for computers.

Other techniques for improving the mass accuracy and sensitivity of the MALDI-TOF MS can be used to analyze the fragments of protein obtained on a collection membrane. These include, but are not limited to, the use of delayed ion extraction, energy reflectors, ion-trap modules, and the like. In addition, post source decay and MS-MS analysis are useful to provide further structural analysis. With ESI, the sample is in the liquid phase and the analysis can be by ion-trap, TOF, single quadrupole, multi-quadrupole mass spectrometers, and the like. The use of such devices (other than a single quadrupole) allows MS-MS or MS" analysis to be performed. Tandem mass spectrometry allows multiple reactions to be monitored at the same time.

Capillary infusion may be employed to introduce the marker to a desired mass spectrometer implementation, for instance, because it can efficiently introduce small quantities of a sample into a mass spectrometer without destroying the vacuum. Capillary columns are routinely used to interface the ionization source of a mass spectrometer with other separation techniques including, but not limited to, gas chromatography (GC) and liquid chromatography (LC). GC and LC can serve to separate a solution into its different components prior to mass analysis. Such techniques are readily combined with mass spectrometry. One variation of the technique is the coupling of high performance liquid chromatography (HPLC) to a mass spectrometer for integrated sample separation/and mass spectrometer analysis.

Quadrupole mass analyzers may also be employed as needed to practice the invention. Fourier-transform ion cyclotron resonance (FTMS) can also be used for some invention embodiments. It offers high resolution and the ability of tandem mass spectrometry experiments. FTMS is based on the principle of a charged particle orbiting in the presence of a magnetic field. Coupled to ESI and MALDI, FTMS offers high accuracy with errors as low as 0.001%.

Surface-Enhanced Laser Desorption/Ionization (SELDI)

In embodiments, the mass spectrometric technique for use in the invention is "Surface Enhanced Laser Desorption and Ionization" or "SELDI," as described, for example, in U.S. Pat. Nos. 5,719,060 and 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe.

SELDI has also been called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen comprise surfaces having chromatographic or biospecific adsorbents attached thereto at addressable locations. Ciphergen's ProteinChip® arrays include NP20 (hydrophilic); H4 and H50 (hydrophobic); SAX-2, Q-10 and (anion exchange); WCX-2 and CM-10 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC 3 and IMAC 30) or O-methacryloyl-N,N-bis-carboxymethyl tyrosine functionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003-0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Application Publication No. US 2003/-0218130 A1 (Boschetti et al., "Biochips With Surfaces Coated With Polysaccharide-Based Hydrogels," Apr. 14, 2003) and U.S. Pat. No. 7,045,366 (Huang et al., "Photocrosslinked Hydrogel Blend Surface Coatings" May 16, 2006).

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has antibodies that bind the biomarkers. After washing the adsorbent to remove unbound material, the biomarkers are eluted from the solid phase and detected by applying to a SELDI biochip that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Antibodies

As reported herein, antibodies that specifically bind a marker (e.g., of a microglial cell or precursor thereof) are useful in the methods of the invention, including methods of detection and therapeutic methods. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. As used herein, the term "antibody" means not only intact antibody molecules, but also fragments of antibody molecules that retain immunogen-binding ability. Such fragments are also well known in the art and are regularly employed both in vitro and in vivo. Examples of antibody fragments include, but are not limited to, Fab, Fab', F(ab')2, and Fv fragments, linear antibodies, scFv antibodies, single-domain antibodies, such as camelid antibodies (Riechmann, 1999, Journal of Immunological Methods 231: 25-38), composed of either a VL or a VH domain which exhibit sufficient affinity for the target, and multispecific antibodies formed from antibody fragments.

The antibodies in the present invention may exist in a variety of forms including, for example, polyclonal antibodies, monoclonal antibodies, Fv, Fab and F(ab')2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). For example, F(ab')2, and Fab fragments that lack the Fc fragment of an intact antibody, clear more rapidly from the circulation, and may have less non-specific tissue binding than an intact antibody (Wahl et al., J Nucl. Med. 24:316-325 (1983). Thus, the antibodies of the invention comprise, without limitation, whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062,1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making and using unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In various embodiments, an antibody is monoclonal. Alternatively, the antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')2" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Methods of preparing antibodies are well known to those of ordinary skill in the science of immunology. Antibodies can be made by any of the methods known in the art utilizing a soluble polypeptide, or immunogenic fragment thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding polypeptides or immunogenic fragments thereof, can be provided to the host in a delivery vehicle that is taken up by immune cells of the host. The cells will in turn express the polypeptide thereby generating an immunogenic response in the host. Alternatively, nucleic acid sequences encoding human polypeptides or immunogenic fragments thereof, can be expressed in cells in vitro, followed by isolation of the polypeptide and administration of the polypeptide to a suitable host in which antibodies are raised.

Alternatively, antibodies may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Hematopoietic Cell Transplantation (HCT)

Hematopoietic Cell Transplantation (HCT) is a promising approach that has the potential to treat peroxisomal disease patients (e.g., adrenoleukodystrophy, adrenomyeloneuropathy, and Zellwger disease). HCT may involve administration of Hematopoietic Stem Cells (HSCs). Hematopoietic Stem Cell (HSC)-based gene therapy may be preceded by a conditioning step (e.g., administering an alkylating agent busulfan), which ablates functionally-defined brain-resident microglia precursors, thereby enhancing engraftment.

HCT is applied to males (boys, men) who have early yet definite evidence of cerebral disease as determined by brain magnetic resonance imaging (MRI). A timely diagnosis is unlikely to occur in males identified from disease signs and symptoms because of the rapidly progressive character of cerebral X-ALD, the expected delays in performing medical evaluations, and confirming the diagnosis. However, boys less than 15 years of age diagnosed with X-ALD because of positive family history yet still symptom free can and should be monitored serially for the earliest evidence of demyelination. These monitoring tests include gadolinium-enhanced brain MRI scans at intervals of 6 months or less to evaluate for cerebral demyelination on T2-weighted images, neuropsychological measures, and endocrinologic tests to evaluate for adrenal insufficiency (ie, Addison's disease). An MRI severity score as low as 2-3 and/or gadolinum enhancement in a boy less than 10 years of age with X-ALD, is highly predictive (approaching 90%) of subsequent progressive cerebral demyelination. It is strongly suggested that such boys undergo HCT as soon as possible. Conversely, boys without evidence of abnormality on brain MRI should be monitored and not transplanted given the likelihood of not developing childhood cerebral form of X-ALD.

The 5 to 10-year follow-up of boys with childhood-onset cerebral X-ALD shows the long-term beneficial effect of HCT when the transplant is done at an early stage of disease. Outcome measures included neuroradiologic assessment of demyelination, neurologic examination, and neurocognitive testing including verbal intelligence and performance (non-verbal) abilities. Unfortunately, the typical boy with parietal-occipital demyelination who is diagnosed due to clinical symptomatology (ie, not at an early stage of disease) has relatively spared verbal intelligence, visual processing difficulties, neurologic impairments in one or more of the following areas—vision, hearing, speech, and gait; and an MRI severity score always >7 and usually ≥11. The HCT and disease-specific outcomes in these boys have been very discouraging with many dying of progressive ALD. For survivors, there are permanent, severe neurologic, and neuropsychologic sequelae; quality of life is compromised. Clearly, as currently practiced, HCT has not been successful for these patients.

Viral Vectors

Retroviral and lentiviral vectors are suitable delivery vehicles for the stable introduction of genes of interest into the genome of a broad range of target cells. Many vector designs have been optimized for maximum transduction efficiency and transgene expression by including FLAP, RRE, and HPRE or WPRE sequences. In particular, those having ordinary skill in the art often include posttranscriptional regulatory sequences to increase transgene expression.

In particular embodiments, vectors of the invention lack or do not comprise a posttranscriptional regulatory element such as a WPRE or HPRE because in some instances these elements increase the risk of cellular transformation and/or do not substantially or significantly increase the amount of mRNA transcript or increase mRNA stability. Therefore, in some embodiments, vectors of the invention lack or do not comprise a WPRE or HPRE as an added safety measure.

The present invention further provides transfer vectors, which may be used to practice methods of the present invention.

While the skilled artisan will appreciate that such transfer vectors may be produced using a variety of different viral vectors, in particular embodiments, the transfer vector is a retroviral vector or a lentiviral vector, in part since lentiviral vectors are capable of providing efficient delivery, integration and long term expression of transgenes into non-dividing cells both in vitro and in vivo. A variety of lentiviral vectors are known in the art, see Naldini et ah, (1996a, 1996b, and 1998); Zufferey et al, (1997); Dull et al, 1998, U.S. Pat. Nos. 6,013,516; and 5,994,136, any of which may be adapted to produce a transfer vector of the present invention. In general, these vectors are plasmid-based or virus-based, and are configured to carry the essential sequences for transfer of a nucleic acid encoding a therapeutic polypeptide into a host cell.

The lentiviral genome and the proviral DNA include three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNAs, respectively. Lentiviruses have additional genes including vif, vpr, tat, rev, vpu, nef and vpx. Adjacent to the 5' LTR are sequences necessary for reverse transcription of the genome (the tRNA primer binding site) and for efficient encapsidation of viral. RNA into particles (the Psi site).

In further embodiments, the lentiviral vector is an HIV vector. Thus, the vectors may be derived from human immunodeficiency-1 (HIV-1), human immunodeficiency-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), caprine arthritis encephalitis virus (CAEV) and the like. HIV based vector backbones (i.e., HIV cis-acting sequence elements and HIV gag, pol and rev genes) are generally be preferred in connection with most aspects of the present invention in that HIV-based constructs are the most efficient at transduction of human cells.

In various embodiments, the vectors of the invention comprise a promoter operably in a microglial cell operably linked to a gene encoding a polypeptide that provides therapy for adreno leukodystrophies and/or adrenomyeloneuropathies. The vectors may have one or more LTRs, wherein either LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (Ψ) packaging signal, RRE), and/or other elements that increase therapeutic gene expression (e.g., poly (A) sequences), except that the vectors of the invention do not comprise a WPRE or HPRE.

In a particular embodiment, the transfer vector of the invention comprises a left (5') retroviral LTR; a central polypurine tract/DNA flap (cPPT/FLAP); a retroviral export element; a promoter active in a microglial cell, operably linked to a polynucleotide encoding an ATP-binding cassette, sub-family D, member 1 (ABCD1) polypeptide; and a right (3') retroviral LTR; wherein the vector does not comprise a woodchuck post-transcriptional regulatory element (WPRE).

In a particular embodiment, the transfer vector of the invention comprises a left (5') retroviral LTR; a retroviral export element; a promoter active in a microglial cell, operably linked to a polynucleotide encoding an ATP-binding cassette, sub-family D, member 1 (ABCD1) polypeptide; a right (3') retroviral LTR; and a poly (A) sequence, wherein the vector does not comprise a woodchuck post-transcriptional regulatory element (WPRE). In another particular embodiment, the invention provides a *lenti* viral vector comprising: a left (5') LTR; a cPPT/FLAP; an RRE; a MND promoter operably linked to a polynucleotide encoding a human ABCD1 polypeptide; a right (3') LTR; and a polyadenylation sequence; wherein the vector does not comprise a woodchuck post-transcriptional regulatory element (WPRE).

In a certain embodiment, the invention provides a lentiviral vector comprising: a left (5') HIV-1 LTR; a Psi (Ψ) packaging signal; a cPPT/FLAP; an RRE; a MND promoter, operably linked to a cDNA encoding a human ABCD1 polypeptide; a right (3') self-inactivating (SIN) HIV-1 LTR; and a rabbit 0-globin polyadenylation sequence; wherein the vector does not comprise a woodchuck post-transcriptional regulatory element (WPRE).

In another embodiment, the invention provides a vector comprising: at least one LTR; a central polypurine tract/DNA flap (cPPT/FLAP); a retroviral export element; and a promoter active in a microglial cell, operably linked to a polynucleotide encoding an ATP-binding cassette, sub-family D, member 1 (ABCD1) polypeptide; wherein the vector does not comprise a woodchuck post-transcriptional regulatory element (WPRE).

In particular embodiment, the present invention provides a vector comprising at least one LTR; a cPPT/FLAP; an RRE; a MND promoter operably linked to a polynucleotide encoding a human ABCD1 polypeptide; and a polyadenylation sequence; wherein the vector does not comprise a woodchuck post-transcriptional regulatory element (WPRE).

In a certain embodiment, the present invention provides at least one SIN HIV-1 LTR; a Psi (Ψ) packaging signal; a cPPT/FLAP; an RRE; a MND promoter, operably linked to a cDNA encoding a human ABCD1 polypeptide; and a rabbit 0-globin polyadenylation sequence, wherein the vector does not comprise a woodchuck post-transcriptional regulatory element (WPRE).

The skilled artisan would appreciate that many other different embodiments can be fashioned from the existing embodiments of the invention, such that the therapeutic transgene is expressed in microglial cell in a retroviral vector that lacks a WPRE or HPRE element.

The present invention further includes pharmaceutical compositions comprising transduced cells produced according to methods described herein. The compositions of the invention may comprise one or more polypeptides, polynucleotides, vectors comprising same, transduced cells, etc., as described herein, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., other proteins, polypeptides, small molecules or various pharmaceutically-active agents. There is virtually no limit to other components that may also be included in the compositions, provided that the additional agents do not adversely affect the ability of the composition to deliver the intended gene therapy.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In a particular embodiment, a formulation or composition according to the present invention comprises a cell contacted with a combination of any number of polypeptides, polynucleotides, and small molecules, as described herein.

In certain aspects, the present invention provides formulations or compositions suitable for the delivery of viral vector systems (i.e., viral-mediated transduction) including, but not limited to, retroviral (e.g., lentiviral) vectors.

In certain aspects, the present invention provides pharmaceutically acceptable compositions which comprise a therapeutically-effective amount of one or more polynucleotides or polypeptides, as described herein, formulated together with one or more pharmaceutically acceptable carriers (additives) and/or diluents (e.g., pharmaceutically acceptable cell culture medium).

Particular embodiments of the invention may comprise other formulations, such as those that are well known in the pharmaceutical art, and are described, for example, in Remington: The Science and Practice of Pharmacy, 20th Edition. Baltimore, MD: Lippincott Williams & Wilkins, 2000.

The retroviral vectors provide methods of adrenoleukodystrophy gene therapy. Examples of suitable lentiviral vectors for adrenoleukodystrophy gene therapy are found for example in U.S. Pat. Publication No. 2016/0159890, which is incorporated by reference herein. As used herein, the term "gene therapy" refers to the introduction of a gene into a cell's genome. In various embodiments, a viral vector of the invention comprises a promoter that expresses a therapeutic transgene encoding a polypeptide that provides curative, preventative, or ameliorative benefits to a subject diagnosed with or that is suspected of having an adrenoleukodystrophy. The virus can infect and transduce the cell in vivo, ex vivo, or in vitro. In ex vivo and in vitro embodiments, the transduced cells can then be administered to a subject in need of therapy. The present invention contemplates that the vector systems, viral particles, and transduced cells of the invention arecan be use to treat, prevent, and/or ameliorate an adrenoleukodystrophy in a subject.

In various embodiments, the retroviral vectors are administered by direct injection to a cell, tissue, or organ of a subject in need of gene therapy, in vivo. In various other embodiments, cells are transduced in vitro or ex vivo with vectors of the invention. The transduced cells are then administered to a subject having adrenoleukodystrophy.

Cells suitable for transduction and administration in the gene therapy methods of the invention include, but are not limited to stem cells, progenitor cells, and differentiated cells. In certain embodiments, the transduced cells are bone marrow stem cells, umbilical cord stem cells, or mesenchymal stem cells.

Recombinant Polypeptide Expression

In order to express the polypeptides of the invention, DNA molecules obtained by any of the methods described herein or those that are known in the art, can be inserted into appropriate expression vectors by techniques well known in the art. For example, a double stranded DNA can be cloned into a suitable vector by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a polypeptide, or fragment thereof, operatively linked to regulatory sequences, e.g., promoter sequences, terminator sequences, and the like, as defined herein. Recombinant vectors which allow for expression of the genes or nucleic acids included in them are referred to as "expression vectors."

In some of the molecules of the invention described herein, one or more DNA molecules having a nucleotide sequence encoding one or more polypeptides of the invention are operatively linked to one or more regulatory sequences, which are capable of integrating the desired DNA molecule into a prokaryotic host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

After the introduction of one or more vector(s), host cells are usually grown in a selective medium, which selects for the growth of vector-containing cells. Expression of recombinant proteins can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

Methods for Evaluating Therapeutic Efficacy

In one approach, the efficacy of the treatment is evaluated by measuring, for example, the biological function of the treated organ (e.g., neuronal function). Such methods are standard in the art and are described, for example, in the Textbook of Medical Physiology, Tenth edition, (Guyton et al., W.B. Saunders Co., 2000). In particular, a method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. Preferably, the tissue is neuronal tissue and, preferably, the organ is brain.

In another approach, the therapeutic efficacy of the methods of the invention is assayed by measuring an increase in cell number in the treated tissue or organ as compared to a corresponding control tissue or organ (e.g., a tissue or organ that did not receive treatment). Preferably, cell number in a tissue or organ is increased by at least 5%, 10%, 20%, 40%, 60%, 80%, 100%, 150%, or 200% relative to a corresponding tissue or organ. Methods for assaying cell proliferation are known to the skilled artisan and are described, for example, in Bonifacino et al., (Current Protocols in Cell Biology Loose-leaf, John Wiley and Sons, Inc., San Francisco, Calif.). For example, assays for cell proliferation may involve the measurement of DNA synthesis during cell replication. In one embodiment, DNA synthesis is detected using labeled DNA precursors, such as [$^{3H}$]-Thymidine or 5-bromo-2*-deoxyuridine [BrdU], which are added to cells (or animals) and then the incorporation of these precursors into genomic DNA during the S phase of the cell cycle (replication) is detected (Ruefli-Brasse et al., Science 302 (5650):1581-4, 2003; Gu et al., Science 302 (5644):445-9, 2003).

Kits

The invention provides kits for the diagnosis, treatment, and/or prevention of a peroxisomal disease or (e.g., neonatal adrenoleukodystrophy, Zellweger syndrome). In one embodiment, the kit includes a capture reagent (e.g., an antibody or nucleic acid molecule) that specifically binds an metallothionein polypeptide or polynucleotide. In some embodiments, the kit includes a composition containing an isolated hematopoietic stem cell or viral vector capable of expressing a therapeutic polypeptide (e.g., ALDP). In another embodiment, the kit includes a nanoparticle for ablative conditioning of endogenous microglial cells.

In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to a subject having or at risk of developing a neurological disease or disorder of the central nervous system. The instructions will generally include information about the use of the composition for the treatment or prevention of the disease or disorder. In other embodiments, the instructions include at least one of the following: description of the therapeutic agent; dosage schedule and administration for treatment or prevention of a neurological disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Elevated Metallothionein Protein Levels are Indicative of Peroxisomal Disease X-linked adrenoleukodystrophy (X-ALD) is an X-linked inherited condition caused by the deficit in the peroxisomal metabolism chain due to mutations in the ABCD1 gene (Moser, Brain 1997; 120: 1485-508), which encodes for the peroxisomal half-transporter ALD protein (ALDP). Mutations in ABCD1 result in abnormal breakdown of very long chain fatty acids (VLCFA), which predominantly affects adrenal gland and the central nervous system (CNS), where the main pathologic finding is inflammatory demyelination. Subjects carrying ABCD mutations are usually asymptomatic at birth, but they can start manifesting disease-related symptoms during childhood or become symptomatic later in life. Male subjects carrying ABCD mutations can develop two major distinct disease forms: inflammatory cerebral X-ALD (cALD) and adrenomyeloneuropathy (AMN). The age at onset of cALD cannot be predicted, it can happen both in childhood (35% of affected boys develop symptoms by 12 years old) or later in life, resulting in complete disability and premature death within few years after the diagnosis.

AMN instead has a more progressive nature, leading anyhow to severe disability in few years from onset. Female carriers of ABCD mutations frequently develop AMN-like manifestations in adult life. Allogeneic hematopoietic cell transplantation is the only effective therapeutic option for this class of diseases and is currently indicated for cALD boys at first appearance of CNS lesions at brain imaging, but in the absence of overt symptoms (Miller et al. Blood 2011; 118:1971-8; Engelen et al. Orphanet J Rare Dis 2012; 7:51). More recently, transplantation of autologous genetically corrected hematopoietic stem cells was also proven to be safe and effective in boys with early stage cALD (Eichler et al. N Engl J Med. 2017; 377(17):1630-1638). These treatments could be offered in the future to the patients identified by newborn screening for which extensive efforts are ongoing (Wiesinger et al, Appl Clin Genet 2015; 8:109-21; Kemper et al, Genet Med 2017; 19(1): 121-126). However, in the absence of a reliable genotype-phenotype correlation (Kemp et al, Hum Mutat 2001; 18(6): 499-515), timely and predictive identification of subjects at risk of developing the disease, and particularly cALD, only depends on biomarkers. The imaging biomarker employed for cALD, contrast enhancement at brain magnetic resonance imaging (MRI), could be replaced and/or co-adjuvated by biochemical markers of the disease detectable in the peripheral circulation that could reflect the pathology at the level of the CNS, as in the case of other neurodegenerative conditions (Hennecke and Scherzer, Biomark Med 2008; 2(1): 41-53; Sharma et al. Neurochem Int 2013; 63(3): 201-229). X-ALD, and more pronouncedly cALD, share many pathologic and pathogenic features with lysosomal storage disorders (LSDs), such as neuroinflammation and oxidative stress. Thus, whether a peripheral early biomarker of CNS damage and treatment efficacy in LSDs, Metallothioneins (MT) (Cesani et al. Ann Neurol 2014; 75(1): 127-137), could serve as a precocious marker of CNS damage and/or treatment response in X-ALD was assessed.

A prospective study was performed to assess the potential use of metallothioneins (MTs) as biomarker(s) in X-ALD. Althought MTs are differentially expressed during disease progression and therapeutic treatment administrations in patients affected by Metachromatic Leukodystrophy (MLD) and other lysosomal storage disorders (LSDs), as well as in their animals disease models (Cesani et al. Ann Neurol 2014; 75(1): 127-137), their expression has not been characterized in peroxisomal diseases such as X-ALD. The following hypotheses were explored: i) whether elevated MT transcripts could be detected in biological samples from patients carrying ABCD mutations showing overt disease manifestations, and ii) whether early variations in MT gene expression could also be present in patients that are likely to develop severe CNS disease before advanced disease has developed. To address these hypotheses, MT protein and transcript levels were analyzed in CNS and peripheral blood samples from ABCD+/− subjects. Cerebrospinal fluid (CSF) and human brain post-mortem samples were obtained from the National Institute of Child Health and Human Development Brain and Tissue Bank for the Developmental Disorders at University of Maryland, whereas peripheral blood samples (PAX gene full blood) were obtained from patients enrolled in collection protocols at referring institutions.

Figure 1C:
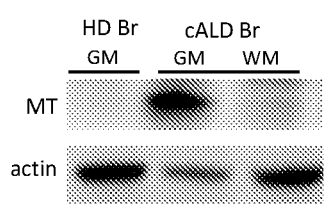
Figure 1D:
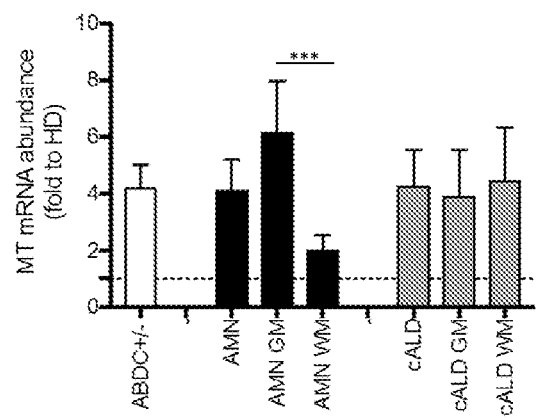
Figure 1E:
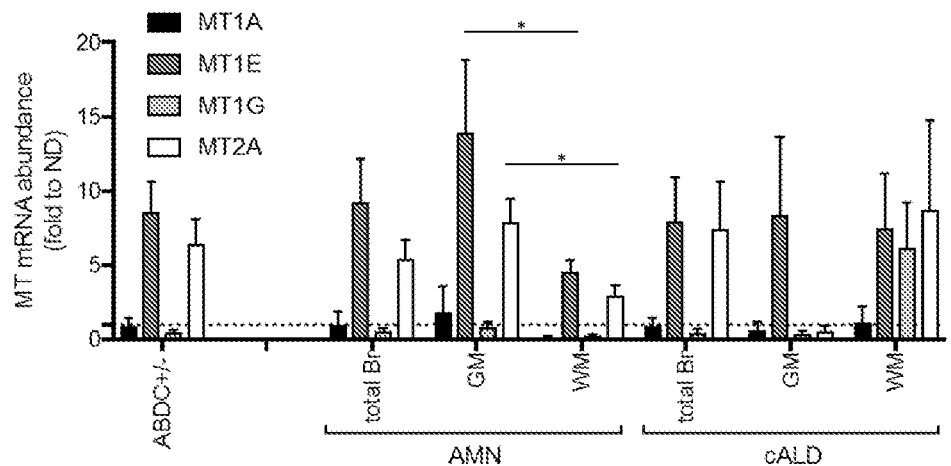

When the presence and quantification of MT protein were assessed in CSF from post-mortem X-ALD and ALD-like samples, accumulation of MT transcripts was detected in the patients' specimens as compared to healthy donors (FIGS. 1A and B). As expected, the higher MT levels were detected in post-mortem CSF from patients affected by Zellweger syndrome, a peroxisomal disorder characterized by inflammatory dysmyelination, also know as neonatal ALD, which is characterized by early perinatal onset and pervasive manifestations. MT protein and transcript levels were tested in post-mortem brain samples from cALD and AMN patients, by analyzing total brain or dissecting white and grey matter (WM and GM, respectively) (FIGS. 1C and D). Accumulation of MT protein (FIG. 1C) and transcripts (FIG. 1D) were also detected in these samplese as compared to healthy donors. There was a more robust MT/MT mRNA presence in the grey versus the white matter of some of the tested samples. Without being bound to theory this is consistent with a neuroprotective role. The contribution of the different MT isoforms to the increased MT mRNA levels detected in patients' brain samples was dissected by examining the expression levels of MT1A, MT1E, MT1G and MT2A (FIG. 1E). Interestingly, in all the tested samples MT1E resulted the most abundant transcript, followed by MT2A. MT1E was expressed more in the AMN grey matter than in the white matter, while no differential expression was noticed in the cALD brains. In cALD brain samples MT2A and MT1G were over-expressed only in the white matter. Without being bound by theory, these differential findings could be interpreted in light of the differential extent and nature of brain involvement in the two conditions. Indeed, pure AMN forms are characterized by lack of brain active myelin damage, but damage to the spinal cord could result in neurodegenerative retrograde insult. cALD is instead characterized by active myelin damage that could be detected as MT transcript increase also, and or specifically in the case of MT1G and MT2A, in the white matter.

Figure 2A:
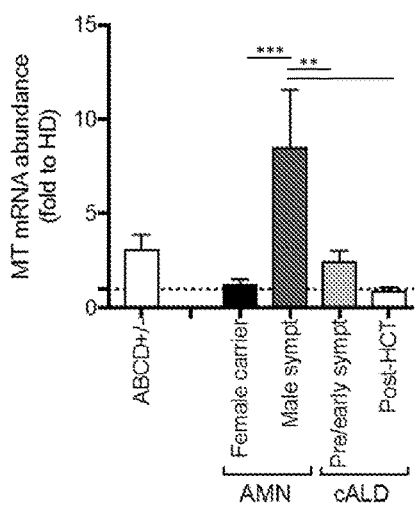
FIGS. 2A-2D show that metallothioneins (MTs) are over-expressed in peripheral blood samples (PAX gene) and T-lymphocytes of patients with cALD and AMN.

In order to assess whether an increase in MT transcript in the CNS could be monitored in peripheral blood cells, MT transcripts in blood (total blood in PaxGene tubes able to stabilize RNA) were analyzed. The samples from ALD patients showed different disease variants and diverse stages of disease progression. Interestingly, MT transcripts accumulated in peripheral blood of ABCD+/− subjects (FIGS. 2A and B). Notably, dissecting these findings according to phenotype allowed the identification of a good correlation between disease burden and MT transcript levels. No increase of MT levels over healthy donor reference values was noticed in asymptomatic female carriers of ABCD mutations; increased MT levels were measured in pre/early symptomatic cALD patients; high levels of MT mRNA were measured in advanced symptomatic AMN male subjects (FIG. 2A).

Figure 2B:
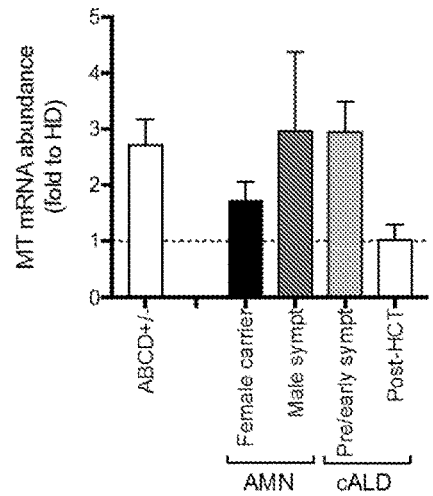
Figure 2C:
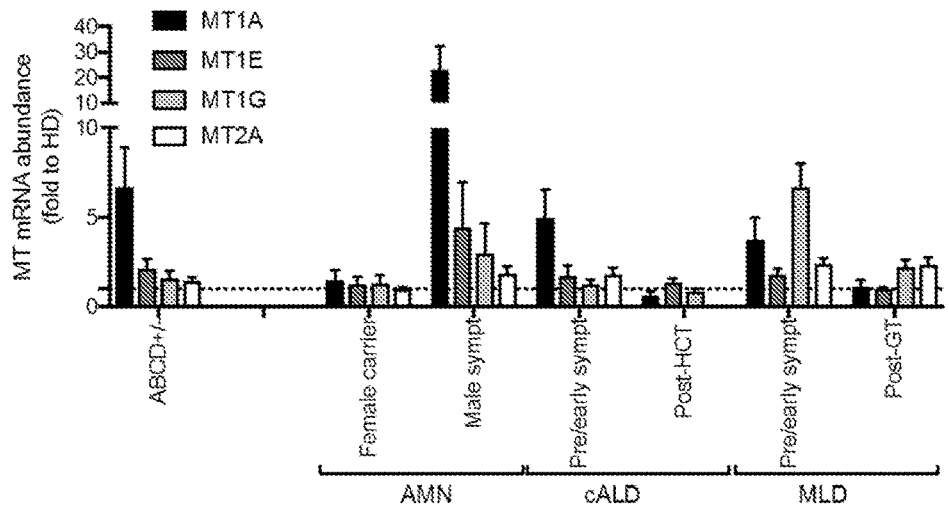
Figure 2D:
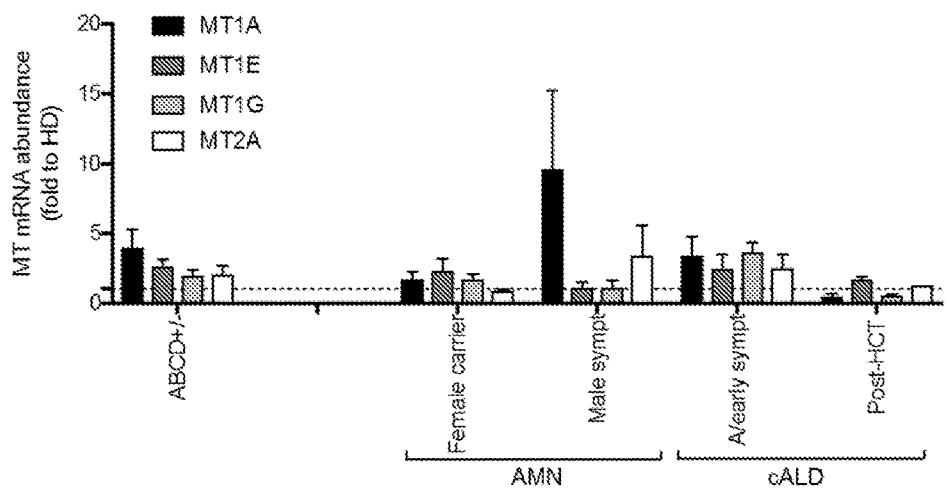

Interestingly, cALD children successfully treated by allogeneic HCT showed MT transcript levels similar to those of healthy donors, demonstrating that both in MLD and cALD MT could serve as a treatment response marker (FIG. 2A). Similar results were obtained in the setting of phytohemagglutinin stimulated T cell lines, a cell source used in a previous biomarker discovery setting (FIG. 2B), only analyzed in the ALD samples. When the contribution of the different MT isoforms to the detected increase in MT mRNA levels was dissected, a unique peripheral blood signature was identified (FIGS. 2C and 2D). Indeed, the most abundant MT isoform in the tested samples was MT1A. Interestingly, this isoform was increased in pre/early symptomatic cALD patients' samples, but not in asymptomatic female carriers (PAX gene data, FIG. 2C). Without being bound by theory, this indicates that MT1A has the potential to be a relevant early indicator of brain disease involvement.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, and accession numbers mentioned in this specification are herein incorporated by reference to the same extent as if each independent patent, publication, and accession number was specifically and individually indicated to be incorporated by reference.

What is claimed is:

1. A method of treating a peroxisomal disease in a selected subject, the method comprising administering a peroxisomal disease treatment to the subject, wherein the subject is selected by detecting an increase in the level of a metallothionein (MT) polynucleotide or polypeptide in a sample of the subject relative to a reference, wherein the peroxisomal disease is adrenoleukodystrophy, neonatal adrenoleukodystrophy, adrenomyeloneuropathy, or Zellweger syndrome, wherein the peroxisomal disease treatment comprises administering an allogeneic hematopoietic stem cell transplant (HCT) comprising an ABCD1 polynucleotide to the subject.

2. The method of claim 1, wherein the peroxisomal disease comprises cerebral involvement characterized by cerebral lesions, neurodegeneration, neuroinflammation, oxidative stress, and/or cerebral demyelination.

3. The method of claim 1, wherein the metallothionein is one or more of metallothionein-1A (MT1A), metallothionein-1B (MT1B), metallothionein-1E (MT1E), metallothionein-1F (MT1F), metallothionein-1G (MT1G), metallothionein-1H (MT1H), metallothionein-1I pseudogene (MT1Ip or MTE), metallothionein-1L (LT1L or MT1R), metallothionem-1M (MT1M or MT1K), metallothionein-1X (MT1X), metallothionein-2 (MT2), metallothionein-2A (MT2A), metallothionein-3 (MT3), and metallothionein-4 (MT4).

4. The method of claim 1, wherein the HCT is administered to the subject via intracerebral ventricular injection.

5. A method of treating a peroxisomal disease in a selected subject, the method comprising administering a peroxisomal disease treatment to the subject, wherein the subject is selected by detecting an increase in the level of a metallothionein (MT) polynucleotide or polypeptide in a sample of the subject relative to a reference, wherein the peroxisomal disease is adrenoleukodystrophy, neonatal adrenoleukodystrophy, adrenomyeloneuropathy, or Zellweger syndrome, wherein the peroxisomal disease treatment comprises administering a lentiviral, or adenoassociated vector comprising an ABCD1 polynucleotide to the subject.

6. The method of claim 5, wherein the lentiviral or adenoassociated vector is administered to the subject via intrathecal or intravenous administration.

* * * * *